United States Patent [19]

Giese et al.

[11] Patent Number: 5,610,020
[45] Date of Patent: Mar. 11, 1997

[54] RELEASE TAG COMPOUNDS PRODUCING KETONE SIGNAL GROUPS

[75] Inventors: Roger W. Giese, Quincy, Mass.; Samy Abdel-Baky, Cary, N.C.; Linxiao Xu, Cambridge, Mass.

[73] Assignee: Northeastern University, Boston, Mass.

[21] Appl. No.: 598,439

[22] Filed: Feb. 8, 1996

Related U.S. Application Data

[60] Division of Ser. No. 53,608, Apr. 22, 1993, Pat. No. 5,516,931, which is a continuation-in-part of Ser. No. 710,318, Mar. 11, 1985, Pat. No. 5,360,819, which is a continuation-in-part of Ser. No. 344,394, Feb. 1, 1982, Pat. No. 4,709,016.

[51] Int. Cl.$^6$ .................................................. G01N 33/566
[52] U.S. Cl. ........................ 435/7.1; 435/7.2; 435/6; 435/175; 435/183
[58] Field of Search ........................... 435/7.1, 7.2, 6, 435/175, 183

[56] References Cited

U.S. PATENT DOCUMENTS

| | | | |
|---|---|---|---|
| 4,629,689 | 12/1986 | Diamond et al. | 435/7 |
| 4,650,750 | 3/1987 | Giese | 435/7 |
| 4,709,016 | 11/1987 | Giese | 530/389 |

OTHER PUBLICATIONS

Buchet et al., "Le dosage par chromatographie en phase gaseuse des métabolites urinaires du trichloréthylene: l'acide trichloroacétique et le trichloroéthanol," Archives de Maladies Professionelles, de Médecine due Travial et de Sécurité Sociale (Paris), 35:395–402 (1974).

Kawamatsu et al., Eur. J. Med. Chem.–Chim. Ther., 16(4) 355–362 [CA95(21): 187138c (1981)].

Landegren et al., "DNA Diagnostics—Molecular Techniques and Automation," Science 242:229–237 (1988).

Rotman, "Sequencing the entire human genome," Industrial Chemist, pp. 18–21, Dec. 1987.

Rudinger–Adler et al., "Arzneim.–Forsch.", 29(9) 1326–1331 [CA92(5):41712b (1979)].

Senft, "Simple determination of trichloroacetic acid in urine using head space gas chromatography: a suitable method for monitoring exposure to trichloroethylene," Journal of Chromatography 337:126–130 (1985).

*Primary Examiner*—Paul J. Killos
*Attorney, Agent, or Firm*—Weingarten, Schurgin, Gagnebin & Hayes LLP

[57] ABSTRACT

A release tag reagent suitable for use in the chemical analysis of a substance to be detected comprises signal, release, and reactivity groups. A class of release tag compounds that are cleaved to release as signal groups very stable electrophoric ketones which are sufficiently volatile for determination in the gas phase of an analytical reaction mixture is disclosed.

9 Claims, 2 Drawing Sheets

5,610,020

RELEASE TAG COMPOUNDS PRODUCING KETONE SIGNAL GROUPS

GOVERNMENT SUPPORT

Part of this invention was made with government support. Therefore, the U.S. Government has certain rights in this invention.

RELATED APPLICATIONS

This application is a division of application Ser. No. 08/053,608, filed Apr. 22, 1993 now U.S. Pat. No. 5,516,931 which is application is a continuation-in-part of application Ser. No. 06/710,318 filed Mar. 11, 1985, now U.S. Pat. No. 5,366,819, which was a continuation-in-part of application Ser. No. 06/344,394 filed Feb. 1, 1982, now U.S. Pat. No. 4,709,016, the whole of which are hereby incorporated by reference herein.

FIELD OF THE INVENTION

This invention pertains to analytical chemical reagents, and more particularly, to cleavable reagents for labeling molecular species in analytical procedures and subsequently releasing and detecting signal-producing ketone compounds.

BACKGROUND OF THE INVENTION

Chemical signal groups are widely used in chemical analysis to label substances of interest such as analytes, internal standards, comparison substances, and specific binding partners for analytes, so that such materials can be followed, detected, or determined in analytical procedures.

Examples of signal groups include radioactive atoms, fluorescent and luminescent molecules, metal-containing compounds, electron-absorbing groups, enzymes, and light-absorbing compounds Presently-used chemical signal groups suffer from a variety of shortcomings. Radioactive atoms in many cases have short half lives, present safety and disposal problems, and cause compounds containing them to be physically unstable and/or chemically labile. In addition, some radioactive materials do not provide high sensitivity, either because they do not produce a high level of radioactivity or because beta particles produced in the decomposition of the radioactive atoms are quenched by the medium to a substantial extent before they can be detected. Also, a variety of closely related radioactive tracers which might be employed and measured simultaneously in a single system are not available. Nonradioactive signal groups suffer from the deficiencies that the signal can be dependent on the environment of the label, which necessitates careful matching of the matrices of samples and standards if accurate data are to be obtained, that the effective signal can be reduced by any dilution of the sample during the analytical procedure, and that possibilities for using multiple labels simultaneously in a single analytical system are limited because of mutual interferences.

Traditional labels are typically retained on the labeled molecular species, and the presence or amount of the labeled material is determined by measuring the signal from the label while still attached to the remainder of the molecule, and often, in the presence of other constituents of the analytical system. As labeled species frequently contain a variety of moieties which can interfere with the measurement of the desired signal, and in addition, the labeled species cannot always be easily brought into a medium which is optimum for the measurement of the signal from the label, this can constitute a serious limitation on the utility of labels generally in a particular system, or on the use of particular labels which an investigator might wish to use.

An example of such traditional label usage is the common practice of labeling molecules with electron-absorbing groups. The molecules are inherently volatile or are rendered volatile by the labeling operation. They can then be determined in the gas phase by gas chromatography with electron capture detection (GC-ECD) or by GC with detection by electron capture negative ion mass spectrometry (GC-ECNI-MS).

The literature contains a few examples of indirect determinations of analytes by determination of a molecular species produced by decomposition of the analyte or chemical cleavage of a derivative of the analyte. An example of the former is the determination of trichloroacetic acid by decarboxylation and measurement of the resulting chloroform. See Buchet et al., Arch. Mal. Prof. Med. Trav. 35:395–402 (1974); and Senft, J. Chromatogr. 337:126–130 (1985). An example of the latter is the analysis for $T_4$ toxin by formation of the labeled derivative N-(N-pentafluorobenzoyl-Met-Gly)-$T_4$ followed by cyanogen bromide cleavage to produce N-pentaflurorobenzoyl homoserine lactone. See U.S. Pat. Nos. 4,650,750 and 4,709,016 by R. W. Giese.

Another example of an indirect determination of an analyte is shown in U.S. Pat. No. 4,629,689 of Diamond. This reference discloses analytical schemes in which, at the conclusion of a selective binding assay, an enzyme is present in a concentration and/or activity which is related to the amount of analyte present in the sample, and this enzyme is measured by measuring the amount of a readily detectable signal group released from a cleavable conjugate of the signal group and another molecular species by the action of the enzyme. As an example, the enzyme β-galactosidase was determined by measuring the amount of o-nitrophenol released by the enzyme-catalyzed cleavage of o-nitrophenyl-β-D-galactopyranoside.

It is very desirable to have labeling reagents which do not suffer from many or most of the above-described disadvantages of traditional reagents, and most importantly, permit multiple species to be labeled and determined in a single sample. Such reagents are the subject of the present application.

SUMMARY OF THE INVENTION

A new class of labeling reagents has recently been conceived, and is undergoing continued development. These reagents, called "release tags," are basically three-part molecules which can be illustrated by the generic formula Sg-Re-Rx in which Sg represents a "signal" group which may be determined readily by an analytical detection device, Rx represents a "reactivity" group containing a functional group which reacts with a substance to be labeled, thereby attaching the release tag, and Re represents a "release" group at which cleavage can occur at an appropriate time and under appropriate conditions to release the signal group Sg in a form suitable for determination.

The three-part nature of release tags permits a wide variety of such materials to be prepared by varying each of the segments. Particularly where the signal groups Sg contain electrophilic atoms and thereby are electrophoric (electron-absorbing in the gas phase), large numbers of closely-related release tag compounds can be prepared by selecting various combinations of the electrophilic atoms and substituent groups for incorporation into Sg. The reactivity groups Rx can also be varied widely to provide release tags capable of bonding specifically and selectively to particular substances to be labeled, or to particular classes of such substances, as desired. Finally, the release groups Re can be varied widely to provide release tags which can be cleaved under particular desired conditions to release signal group-containing molecules for analytical detection or determination.

The totality of these features is thus seen to provide the potential for a vast multiplicity of release tags, each of which can ultimately release a signal group different from those of other release tags. In principle, each of a series of many substances can be separately labeled with a different release tag. Subsequently the labeled substances can be brought together and employed as a combined, analytical reagent. Since the "signal" molecules can be released and determined simultaneously, a large number of analytes in the sample can be measured simultaneously. Release tags are thus seen to be extremely powerful analytical tools.

Examples of analytical undertakings in which release tags will be of great value are the human genome project, testing for infectious diseases such as AIDS, and genetic screening. The need for multiple labels for such purposes has been expressed. See e.g., Landegren, U., Kaiser, R., Caskey, C. T. and Hood, L., "DNA Diagnostics-Molecular Techniques and Automation", Science 242:229–237 (1988); Rotman, D., "Sequencing the Entire Human Genome" Industrial Chemist, December 18–26, 1987; Giese, R. W., "Electrophoric Release Tags: Ultrasensitive Molecular Labels Providing Multiplicity", Trends in Anal. Chem. 2:166–168 (1983).

The present application relates to a class of release tag conpounds that are cleaved to release as signal groups very stable electrophoric ketones which are sufficiently volatile for determination in the gas phase of an analytic reaction mixture. The compounds have the general formula:

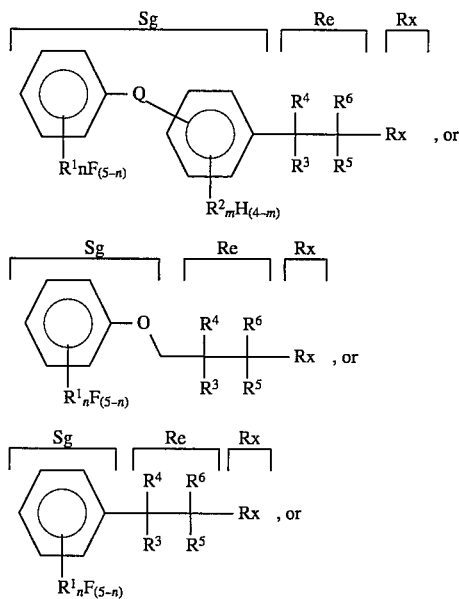

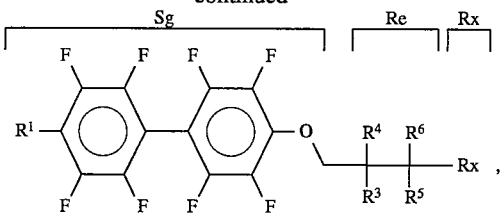

where the correspondence with the generic formula given above is indicated.

In the compounds of the invention $R^1$=H, $CF_3$, R, or OR (n=0 to 2);

$R^2$=H, D, or F (m=0 to 4); $R^2$=R, OR, $NR_2$ (m=0 to 2); or $R^2$ plus $R^3$=Z;

$R^3$=R, or $R^2$ plus $R^3$=Z;

Z=o-phenylene or propylene as part of a five- or six-membered ring which can contain one or more of H, D, F, or R;

$R^4$=OH and $C(R^5,R^6)$=carbonyl (C=O) or $R^4$=OH and $R^6$=OH and $R^5$=H or R, or $R^4$–$R^6$=double bond (C=C) and $R^5$=H or R, or $R^4$=OH and $R^5$ and $R^6$ are each selected from H or R;

Q=—$CH_2O$—, —$CH_2N(COR)$—, —CONH—, —CONR—, —CON(COR)—, —$CH_2OAr$—, or —CONHAr—;

R=C1 to C8 alkyl, benzyl, or phenyl which can contain one or more of H, D, or F;

Ar=phenylene or phenyleneoxy or benzyleneoxy which can contain one or more of H, D, F, or R on the aromatic ring; and Rx=reactivity group, where, when $R^4$=OH and $C(R^5,R^6)$=carbonyl, said $C(R^5,R^6)$ carbonyl group may be included within said reactivity group; where, when $R^4$=OH and $R^5$ and $R^6$ are each selected from H or R, Rx comprises a keto group attached to the $C(R^5,R^6)$ group; and where whenever Rx comprises a keto group attached to the $C(R^5,R^6)$ group, Rx can also be represented as CORx' where Rx' makes up part of the reactivity group.

The invention also relates to molecular conjugates in which at least one of the above-described release tag compounds is covalently bound to at least one labelable substance having a reactive site capable of reacting with the reactivity group of the release tag compound, and to chemical assays which employ release tag compounds or conjugates of such compounds with labelable substances.

Additionally, the invention relates to molecular conjugates and to chemical assays in which the release tag compound employed can have any type of releasable signal group but in which the release group is either an α-hydroxyketo group or a β-hydroxyketo group.

The release tags can be used to detect DNA sequences, antigens, and haptens indirectly (by serving as labels for binding partners or binding competitors of these substances), or to detect analytes directly (by reacting directly and covalently with the analytes).

The release tag compounds of the invention are very easily synthesized as a class, e.g., from the corresponding ketone precursor, and the ketone signal groups released upon cleavage of the release tag are inherently volatile and very stable, leading to easy detection in the gas phase. The huge potential variety of signal groups leads to a large multiplicity of target compounds which can be analyzed simultaneously.

BRIEF DESCRIPTION OF THE DRAWINGS

Other features and advantages of the invention will be apparent from the following description of the preferred embodiments thereof and from the claims, taken in conjunction with the accompanying drawings in which.

DESCRIPTION OF THE PREFERRED EMBODIMENTS INVENTION

Figure 1:
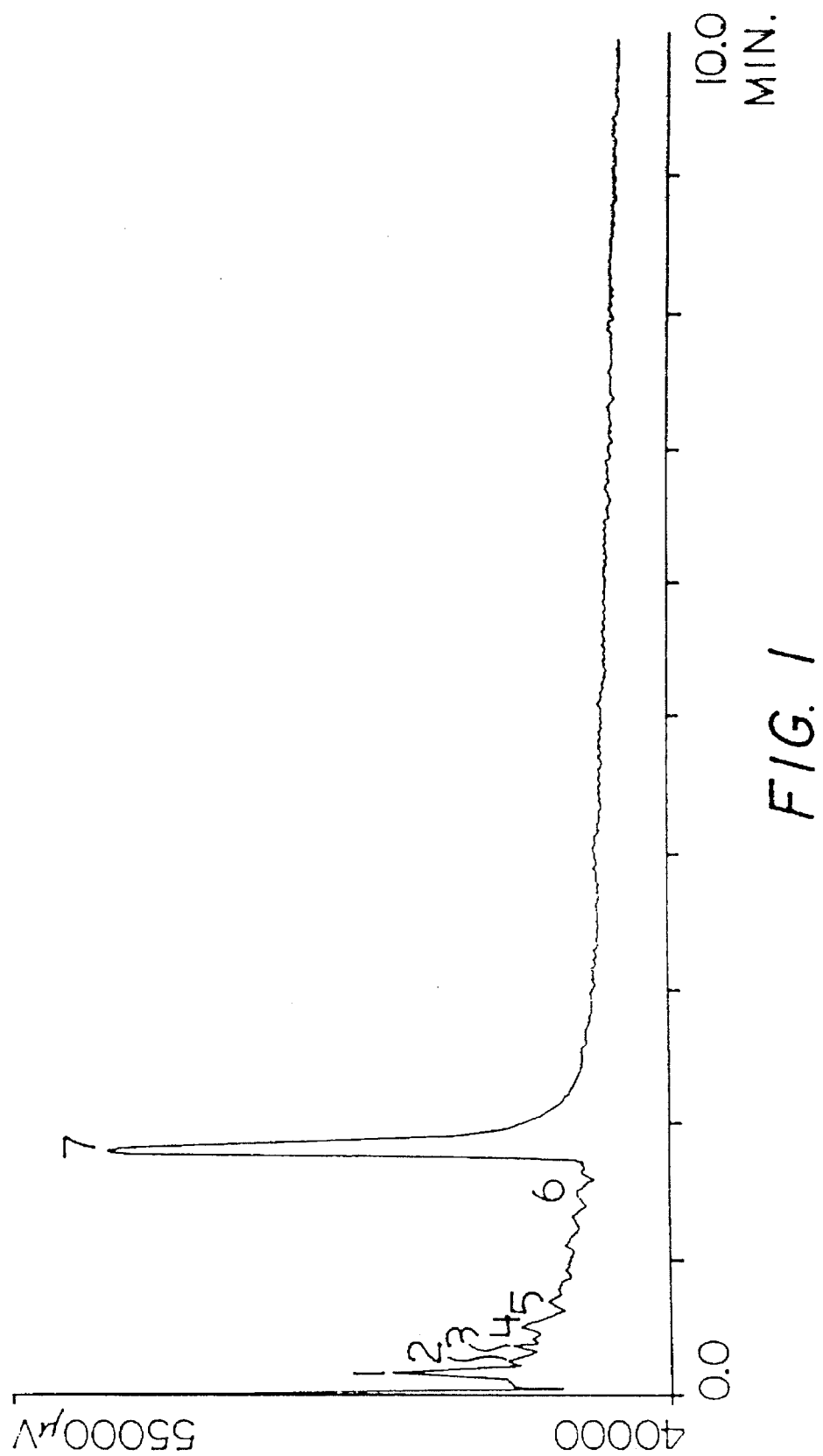
FIG. 1 shows a gas chromatography chromatogram of a signal compound thermally released from a release tag compound of the invention.

Within the general formula for the release tag compounds of the present invention are four specific subclasses of release tag compounds, corresponding to four different classes of the release group (Re). The formulas of members of the subclasses are given below.

a) Olefins, corresponding to the case where $R^4$-$R^6$= double bond (C=C), have the formula

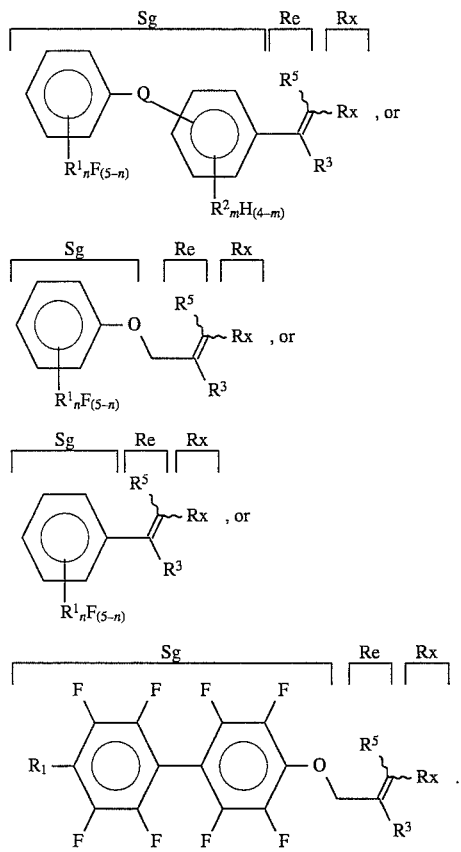

b) Glycols, corresponding to the case where $R^4$=OH and $R^6$=OH, have the formula

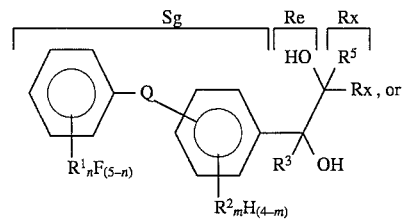

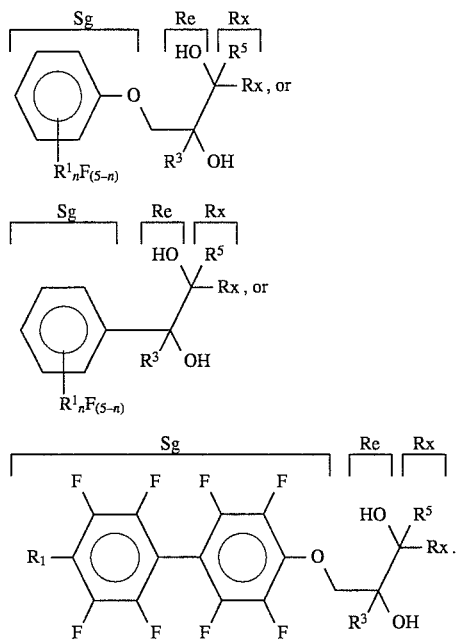

c) α-Hydroxyketos corresponding to the case where $R^4$=OH and $C(R^5,R^6)$=carbonyl (C=O), have the formula

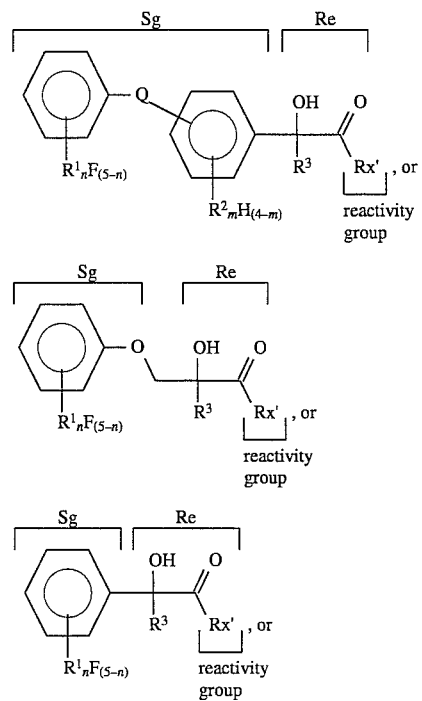

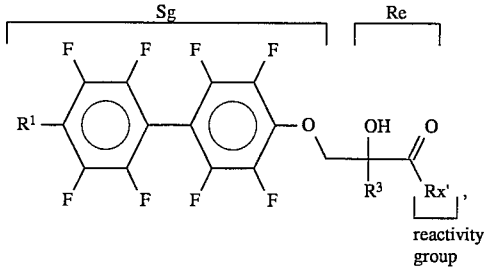

where the $C(R^5,R^6)$ carbonyl group is simultaneously part of the group Re and the reactivity group.

d) β-hydroxyketos, corresponding to the case where $R^4$=OH and $R^5$ and $R^6$ are each selected from H or R, have the formula

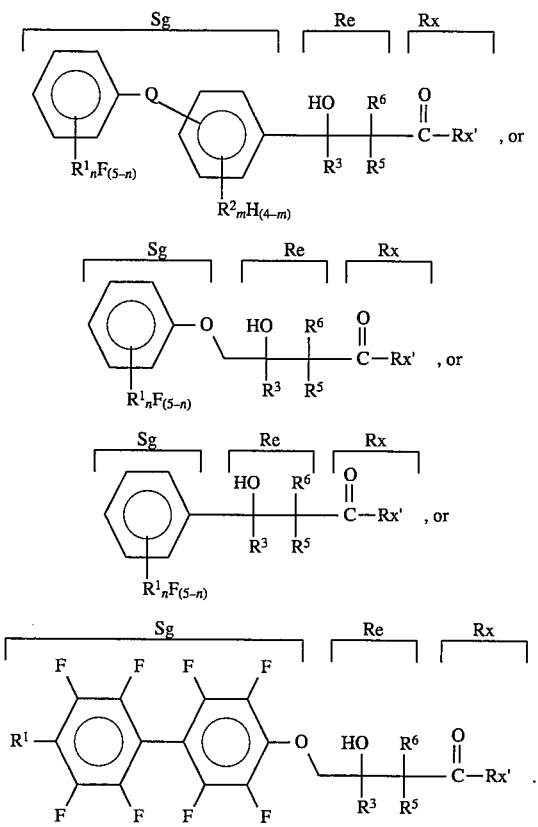

In each of the above subclasses, the indicated terms are defined as previously described. The substituents for the signal group of this class of release tag compounds have been chosen so that they would not ordinarily be contaminated by more than one isotope. Thus, the molecular weight of the released signal can be controlled precisely, and large numbers of closely related release tag compounds can be formed. It is thus seen that the release tag compounds consist of moderately simple molecules bearing different signal, release, and reactivity groups.

The release tag compounds of the invention are useful for labeling any substance, provided that the substance to be labeled possesses at least one functional group capable of reacting with the reactivity group Rx of the release tag compound to be employed. To put it another way, the release tag compounds of the invention make it possible to label a vast number of substances which either possess or can be modified to possess a reactive functional group, by providing one or more release tags with reactive functional groups capable of reaction with the reactive functional groups of the substance to be labeled, and causing these materials to react to form a covalent linkage.

Among the many sorts of substances which are capable in principle of being labeled by the release tag compounds of the invention are materials one wishes to analyze for, generally referred to as analytes, and analogs of such analytes; materials which constitute primary or secondary binding partners for such analytes or analyte analogs; and various substrates for enzymes which are used as labels on analyte analogs and on primary and secondary binding partners for various analytes.

Representative examples of analytes which may be labeled by the release tag compounds of the invention are materials such as a) proteins: for example, protein hormones such as insulin, thyroid stimulating hormone (TSH), growth hormone (GH), follicle stimulating hormone (FSH), and luteinizing hormone (LH); enzymes such as creatine kinase and lactate dehydrogenase (LDH); tumor antigens such as carcinoembryonic antigen (CEA); antibodies such as anti-human immunodeficiency virus (A'HIV), A'hepatitis, IgE, and $IgG_1$; receptors such as progesterone receptor and estrogen receptor; and transport proteins such as α-lipoprotein and transferrin;

b) peptides: for example, hormones such as angiotensin II, glucagon, and adrenocorticotrophic hormone (ACTH);

c) amino acids such as triiodothyronine ($T_3$), tetraiodothyronine or thyroxin ($T_4$) and γ-aminobutyric acid;

d) polynucleotides: for example, gene fragments and genes such as the AIDS gene and the sickle Hb gene; and RNA such as mRNA, tRNA, rRNA;

e) nucleotides such as adenosine monophosphate (AMP);

f) nucleosides such as $N^2$-(dG-8-yl)-2-aminofluorene;

g) nucleobases such as 5-methylcytosine;

h) lipids: for example, steroids such as cortisol, estradiol, and aldosterone; and prostaglandins such as $PGE_2$;

i) carbohydrates such as blood group antigens;

j) drugs such as digoxin and theophylline;

k) cells: for example, lymphocytes such as B lymphocytes and T lymphocytes;

l) viruses such as the hepatitis, HIV-I, and HIV-II;

m) vitamins such as Vitamin A, Vitamin D, Vitamin E, Vitamin $B_{12}$, and folic acid;

n) coenzymes such as AND; and o) bioactive amines such as epinephrine and dopamine.

A primary binding partner for an analyte is a substance that forms a specific noncovalent complex with the analyte. For many types of analytes, corresponding antibodies may be obtained as primary bonding partners. Such analytes are classified into two broad classes based on their sizes—antigens (which are large) and haptens (which are small). Sometimes an antibody is the analyte of interest, in which case the corresponding antigen or hapten is used as the specific binding partner.

Other classes of primary binding partners also exist. A certain nucleic acid (DNA or RNA) or fragment thereof may be an analyte, in which case the complementary nucleic acid (DNA or RNA), generally termed a "DNA probe" when it comprises DNA, is the primary binding partner. An enzyme can be a binding partner for an inhibitor as an analyte, or vice versa. Similarly, lectins bind sugars, avidin and its analogs (e.g., streptavidin and succinylavidin) bind biotin, and receptors bind messenger substances such as hormones and neurotransmitters. As before, either one of the substances in each of these pairs is a primary binding partner for the other.

A secondary binding partner is a substance that binds to a primary binding partner even after the primary binding partner has become bound to its analyte. For example, if antibody $Ab_1$ binds analyte An, forming a complex $Ab_1 \cdot An$, and a second antibody $Ab_2$ is available which binds in turn to the prior complex onto the $Ab_1$ part, forming $Ab_2 \cdot Ab_1 \cdot An$, then $Ab_2$ is a secondary binding partner for the analyte. The binding of $Ab_2$ onto $Ab_1$ is thus "piggyback" in nature. The site on $Ab_1$ that is recognized by $Ab_2$ may either be an inherent part of $Ab_1$, or a hapten or antigen recognized by $Ab_2$ that has been conjugated to $Ab_1$.

Since protein A and protein G bind to antibodies at regions remote from the antibody binding site, they are often used as secondary binding partners in immunoassays.

Biotin commonly is attached to an antibody for an analyte so that avidin (or an avidin analog), which specifically binds to biotin, can function as a secondary binding partner relative to the analyte against which the antibody was developed.

If the conjugate of an antibody $Ab_1$ and avidin (i.e., $Av\text{-}Ab_1$) binds to an analyte An forming the complex $Av\text{-}Ab_1 \cdot An$ and this complex in turn can bind to biotin forming $biotin \cdot Av\text{-}Ab_1 \cdot An$, then biotin is a secondary binding partner for An. Similarly, biotin conjugated to a substance X (i.e., X-biotin) is a secondary binding partner for An if $X\text{-}biotin \cdot Av\text{-}Ab_1 An$ can form.

A hapten can function as a secondary binding partner. For example, a hybrid antibody can be prepared which binds the analyte An in one binding site and a hapten H to another. Thus, hapten H is then a secondary binding partner for An. If hapten H is first conjugated to some other substance X forming H-X, then H-X is a secondary binding partner for An if the complex $An \cdot Ab \cdot H\text{-}X$ forms.

Similarly, if a nucleic acid analyte $NA_A$ is recognized by (hybridizes to) nucleic acid $NA_1$, forming the complex $NA_1 \cdot NA_A$, and nucleic acid $NA_2$ can further bind to this complex by binding to an unused part of $NA_1$, forming $NA_2 \cdot NA_1 \cdot NA_A$, then $NA_2$ is a secondary binding partner relative to $NA_A$.

Proteins such as antibodies, avidin, streptavidin, lectins, protein A, and protein G are commonly used as primary or secondary specific binding proteins. Related forms of these and other proteins are also used, e.g. the Fab, and $F(ab')_2$ parts of antibodies. Succinylavidin is another example.

Polymer-modified proteins may also be used as primary or secondary binding partners. Examples of the polymers employed in producing such polymer-modified proteins are other proteins, polypeptides, polysaccharides, polynucleotides, and synthetic polymers such as polyacrylic acid or polyacrylylhydrazide. In use, the polymer on the polymer-modified protein carries many copies of a given release tag, thus allowing the polymer-modified protein to be detected with high sensitivity. Similarly, polymer-modified polynucleotides can be prepared for detection with very high sensitivity.

Examples of primary and secondary binding partners which are conveniently labeled by the release tag compounds of the invention are a) proteins: for example, antibodies, avidin, streptavidin, lectins, protein A, and protein G;

b) polymer-modified proteins: for example, antibody-polyasp-hydrazide, antibody-dextran, antibody-polyethyleneimine, antibody-dextran, avidin-dextran, and avidin-polyglu-hydrazide;

c) peptides: for example, angiotensin II;

d) polynucleotides: for example, complementary DNA and RNA;

e) polymer-modified polynucleotides: for example, 3'-tailed DNA and RNA, DNA-polyglu-hydrazide, and DNA-dextran hydrazide;

f) carbohydrates: for example, glucose;

g) haptens: for example, digoxin, digoxigenin, and fluorescein; and h) biotin.

Many of the above-listed materials can function either as primary or secondary binding partners, depending on the assay being conducted.

Examples of enzyme substrates which may be labeled by the release tag compounds of the invention are: carbohydrates such as chitin and glycolchitin, dextran, glucose-6-phosphate, and galactose glycosides; lipids such as cholesterol esters; nucleotides such as ATP and AMP; polynucleotides such as DNA and RNA; peptides such as dipeptides and dipeptide esters; proteins such as albumin; and esters such as p-nitrophenyl esters, phosphate esters, and carboxylic acid esters.

As explained above, the release tag compounds of the invention are capable of forming conjugates with a wide variety of other substances. Such conjugates are fully covalent materials in which at least one release tag compound is covalently linked to at least one other molecular moiety. Conjugates may thus be symbolized as $(\text{substance})_u(\text{tag})_t$, where the tag is a residue of a release tag which is covalently bound to the substance. The subscripts u and t indicate that depending on the particular release tags and substances chosen for the conjugate, conjugates may contain one release tag and one other substance to be labeled, one release tag and multiple other substances, one substance labeled by multiple release tags, and multiple substances labeled with multiple release tags. The substance being labeled may possess multiple reactive functional groups initially, not all of which are necessarily reacted with release tag compounds in forming the conjugate.

In conjugates containing multiple release tag residues, these residues can be derived from the same or different release tag molecules. Similarly, where the conjugate contains multiple subunits, as in a protein possessing quaternary structure, these may also be the same or different.

One can also use a release tag to label a linking reagent, forming a (release tag)$^n$-linking reagent conjugate (n≧1). The (release tag)$^n$-linking reagent then is attached via a reactivity group on the linking reagent to a substance of interest such as the analyte, analyte analog, or specific binding partner (primary or secondary) for the analyte. Thus the linking reagent provides two useful properties. First, it provides a different reactivity group for attaching a given release tag to the substance of interest. Second, it can be employed to increase the number of release tags attached to a substance of interest, thereby increasing the sensitivity of an assay.

The release tag compounds of the invention are synthesized using principles and reactions which are well known to those skilled in the art. They are prepared basically in three stages. In the first stage (stage one), molecular species containing the signal group Sg, the release group Re, and the reactivity group Rx in final or precursor form (i.e., carrying a protecting group) are obtained either commercially or via synthesis. The second stage (stage two) involves carrying out appropriate chemical reactions to join these materials into the release tag compound SgReRx which may, however, still contain certain functionalities in precursor or protected form. In the third stage (stage three), any such functionalities are converted to the desired final form. The reactivity groups Rx or their precursors for stage three are generally commercially available because of the widespread usefulness of such reactivity groups in bio-organic chemistry.

For synthesis of the release tag compounds of the preferred embodiments of the invention, where the release group consists of an olefin, glycol, α-hydroxyketo, or β-hydroxyketo compound, this functionality is established either before or after incorporation of the release group precursor into a release tag by reactions such as oxidation, addition (both nucleophilic and electrophilic addition of double bonds), hydrolysis, olefination reaction (e.g. Wittig reaction and Horner-Emmons reaction), or combinations of these. For the formation of olefin release tags, the general strategy is to start with an electrophoric ketone which is obtained either commercially or via synthesis. The ketone then can be converted into an olefin by a Wittig reaction, a Horner-Emmon's reaction, or a Peterson reaction (March, J., *Advanced Organic Chemistry*, 4th Edn., Wiley, New York, 1992, pp. 956 and 952.). In turn, a glycol release group can be formed by hydroxylation of the olefin with alkaline potassium permanganate, or osmium tetraoxide in pyridine, or other reagents as described (March, J., Ibid., p. 822). An addition reaction onto the ketone can afford the corresponding β-hydroxy carbonyl compound, such as a β-hydroxy ester. An aldol condensation reaction under basic or acidic conditions also can be used (March, J., Ibid., pp. 937, 944, and 945.). α-Hydroxy keto compounds, for example, α-hydroxy acids, can be obtained either by hydrolysis of α-hydroxy nitriles or α-halo acids (March, J., Ibid., pp. 370 and 887). Related procedures for synthesizing olefinic, glycol, α- and β-hydroxyketo compound release tags can be developed from standard reactions in organic chemistry by one skilled in the art.

A reactivity group is then incorporated, taking advantage of an appropriate functional group introduced in the above mentioned reactions. Usually the reactivity group comprises or is synthesized from a carboxylic acid by well-known methods.

The volatile compound derived from the Sg moiety in a release tag is detected preferably by an electron capture detector (ECD) or by electron capture negative ion mass spectrometry (ECNI-MS). Examples of other gas phase detectors that may be used are as follows: flame ionization detector, electron impact MS, positive ion chemical ionization MS, thermospray MS, fast atom bombardment MS, particle beam MS, electrospray MS, plasma desorption MS, laser ionization MS, laser desorption MS, laser desorption-ionization (±matrix) MS, laser (or thermal) desorption electron capture MS, thermal conductivity detector, nitrogen-phosphorous detector, photoionization detector, flame photometric detector, and ion mobility detector.

The following examples are presented to illustrate the advantages of the present invention and to assist one of ordinary skill in making and using the same. These examples are not intended in any way otherwise to limit the scope of the disclosure.

EXAMPLE I

Several series of novel ketones are useful as Sg precursors for preparing release tag compounds of the invention. These volatile, electrophoric ketones are released as signal groups upon cleavage of the corresponding release tag compound. Their structure and mode of synthesis are given below. The solvent for all the NMR spectra was CDCl$_3$. Preparative gas chromatography (PGC) was done on a 6'×14" aluminum column (packed with 20% SE-30/Chromosorb W (NAW, 60–80 mesh)).

Ketones 1–16

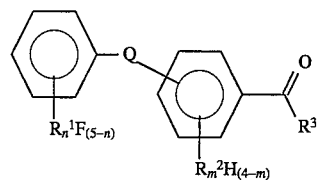

(1) Synthesis of ketones with Q = —CH$_2$O—:

| No. | R$^1$ | R$^2$ | R$^3$ | Q |
|---|---|---|---|---|
| 1 | / | / | CH$_3$ | 4'-CH$_2$O |
| 2 | / | 3'-CH$_3$ | CH$_3$ | 4'-CH$_2$O |
| 3 | / | 3'-CH$_3$ 5'-CH$_3$ | CH$_3$ | 4-CH$_2$O |
| 4 | / | 3'-OCH$_3$ | CH$_3$ | 4'-CH$_2$O |
| 5 | / | 3'-OCH$_3$ 5'-OCH$_3$ | CH$_3$ | 4'-CH$_2$O |
| 6 | / | 3'-F | CH$_3$ | 4'-CH$_2$O |
| 7 | / | 3'-F 5'-F | CH$_3$ | 4'-CH$_2$O |
| 8 | / | 2'-F 3'-F 5'-F | CH$_3$ | 4'-CH$_2$O |
| 9 | / | 2'-F 3'-F 5'-F 6'-F | CH$_3$ | 4'-CH$_2$O |
| 10 | / | 3'-OC$_2$H$_5$ | CH$_3$ | 5'-CH$_2$O |
| 11 | / | 3'-OCD$_3$ | CH$_3$ | 5'-CH$_2$O |
| 12 | / | 3'-OCH$_2$C$_6$F$_5$ | CH$_3$ | 5'-CH$_2$O |
| 13 | / | / | C$_2$H$_5$ | 4'-CH$_2$O |
| 14 | / | CH$_2$CH$_2$CH$_2$* | | 5'-CH$_2$O |
| 15 | / | o-Phenylene* | | 4'-CH$_2$O |
| 16 | OCH$_3$ | / | CH$_3$ | 4'-CH$_2$O |

*R$^2$, R$^3$

General procedure for synthesis of compounds 1, 2, 4, 5, 13–15:

A mixture of hydroxy aromatic ketone (5 mmol), pentafluorobenzyl bromide (1.3 g, 5 mmol), potassium carbonate (5 g), acetone (30 ml), and 18-crown-6 ether (0.1 g) were stirred under reflux for 5 hours. After addition of some Celite 521, the reaction mixture was filtered and the residue was washed with acetone three times. Then the filtrate was evaporated on a rotary evaporator (rotavapor). The product was purified by recrystallization (hexane/ether or hexane/ethyl acetate). The yields and m.p. and the spectral data are as follows:

4'-Pentafluorobenzyloxyacetophenone (1):

Yield: 90%. m.p. 88°–89° C. $^1$H NMR, δ: 2.56 (s, 3H, CH$_3$), 5.20 (s, 2H, CH$_2$O), 7.02 (d, 2H, J=8.8 Hz, H—C3' & H—C5'), 7.96 (d, 2H, J=8.8 Hz, H—C2' & H—C6') ppm; $^{13}$C NMR, δ: 26.1 (CH$_3$), 57.3 (CH$_2$O), 109.5 (C1", $^2$J$_{C-F}$=8 Hz), 114.2 (C3' & C5'), 130.5 (C2' & C6'), 131.1 (C1'), 137.5 (C2" & C6", J$_{C-F}$=248 Hz), 141.8 (C4",J$_{C-F}$=256 Hz), 145.6 (C3" & C5", J$_{C-F}$=251 Hz), 161.5 (C4'), 196.4 (C=O) ppm. MS(EI): 316(M$^+$); MS (ECNI): 135([M-PFBz]$^-$, 100%).

3'-Methyl-4'-pentafluorobenzyloxyacetophenone (2):

Yield: 88%. m.p. 120°–121° C. $^1$H NMR, δ: 2.21 (s, 3H, CH$_3$—C3'), 2.56 (s, 3H, CH$_3$CO), 5.22 (s, 2H, CH$_2$O), 7.00 (d, 1H, J$_{5-6}$=8.4 Hz, H—C5'), 7.78 (bs, 1H, H—C2'), 7.84 (d, 1H, J$_{6-5}$=8.4 Hz, H—C6') ppm: $^{13}$C NMR, δ: 16.1 (CH$_3$ on C3'), 26.3 (CH$_3$CO), 57.6 (CH$_2$O), 109.8 (C1", $^2$J$_{C-F}$=18

Hz) 110.3 (C5') 127.4 (C1'), 130.8 (C2'), 131.2 (C6'), 137.5 (C2" & C6", $J_{C-F}$=254 Hz), 141.8 (C4", $J_{C-F}$=256 Hz), 145.7 (C3" & C5", $J_{C-F}$=254 Hz), 159.9 (C4'), 196.9 (C=O) ppm. MS(EI): 330 (M$^+$); MS(ECNI): 149 ([M-PFBz]$^-$, 100%).

3'-Methoxy-4'-pentafluorobenzyloxyacetophenone (4):

Yield: 90%. m.p. 110°–111° C. $^1$H NMR, δ: 2.55(s, 3H, CH$_3$CO), 3.87 (s, 3H, CH$_3$O), 5.21 (s, 2H, CH$_2$O), 7.00 (d, 1H, $J_{5-6}$=8.0 Hz, H—C5'), 7.44–7.57 (m, 2H, H—C2' & H—C6') ppm; $^{13}$C NMR, δ: 26.1 (CH$_3$CO), 55.9 (CH$_3$O), 58.5 (CH$_2$O), 109.5 (C1", $^2J_{C-F}$=17 Hz), 110.8 (C2'), 113.0 (C5'), 122.7 (C6'), 131.8 (C1'), 137.5 (C2" & C6", $J_{C-F}$=254 Hz), 141.8 (C4", $J_{C-F}$=255 Hz), 145.7 (C3" & C5", $J_{C-F}$=251 Hz), 149.8 (C3'), 151.4 (C4'), 196.6 (C=O) ppm. MS (EI): 346 (M$^+$); MS(ECNI): 165 ([M-PFBz]$^-$, 100%).

3',5'-Dimethoxy-4'-pentafluorobenzyloxyacetophenone (5):

Yield: 86%. m.p. 119°–120° C. $^1$H NMR, δ2.59 (s, 3H, CH$_3$CO), 3.87 (s, 6H, CH$_3$O), 5.22 (s, 2H, CH$_2$O), 7.18 (s, 2H, H—C2' & H—C6') ppm; $^{13}$C NMR, δ: 26.0 (CH$_3$CO), 55.8 (CH$_3$O), 60.6 (CH$_2$O), 105.2 (C2' & C6'), 110.6 (C1", $^2J_{C-F}$=18 Hz), 133.2 (C1'), 137.0 (C2" & C6", $J_{C-F}$=248 Hz), 139.7 (C3' & C5') 141.2 (C4", $J_{C-F}$=254 Hz), 145.7 (C3" & C5", $J_{C-F}$=254 Hz), 153.1 (C4'), 196.5 (C=O) ppm. MS(EI): 360 (M$^+$); MS(ECNI): 179 ([M-PFBz]$^-$, 100%).

4'-Pentafluorobenzyloxypropiophenone (13):

Yield: 92%. m.p. 71°–72° C. $^1$H NMR, δ: 1.21 (t, 3H, J=7.1 Hz, CH$_3$), 2.96 (q, 2H, J=7.1 Hz, CH$_2$), 5.19 (s, 2H, CH$_2$O), 7.01 (d, 2H, J=8.7 Hz, H—C3' & H—C5'), 7.97 (d, 2H, J=8.7 Hz, H—C2' & H—C6') ppm; $^{13}$C NMR, δ: 8.1 (CH$_3$), 30.3 (CH$_2$), 57.3 (CH$_2$O), 109.7 (C1", $^2J_{C-F}$=18 Hz), 114.2 (C3' & C5), 130.1 (C2' & C6'), 130.8 (C1'), 137.5 (C2" & C6", $J_{C-F}$=254 Hz), 141.8 (C4", $J_{C-F}$=256 Hz), 145.7 (C3" & C5", $J_{C-F}$=251 Hz), 161.5 (C4'), 199.1 (C=O) ppm. MS(EI): 330 (M$^+$); MS(ECNI): 149 ([M-PFBz]$^-$, 100%).

5-Pentafluorobenzyloxytetralone (14):

Yield: 88%. m.p. 79°–80° C. $^1$H NMR, δ: 2.09 (m, 2H, H$_2$C3), 2.61 (t, 2H, $J_{4-3}$=6.6 Hz, H$_2$C4), 2.84 (t, 2H, $J_{2-3}$=6.1 Hz, H$_2$C2), 5.17 ("s", with fine splitting, CH$_2$O), 7.16 (dd, 1H, $J_{6-7}$=8.1 Hz, $J_{6-8}$=0.9 Hz, H—C6), 7.29 (dd, 1H, $J_{7-6}$=8.1 Hz, $J_{7-8}$=7.8 Hz, H—C7), 7.71 (dd, 1H, $J_{8-7}$=7.8 Hz, $J_{8-6}$=0.9 Hz, H—C8) ppm; $^{13}$C NMR, δ: 22.4 (C3), 22.7 (C4), 38.7 (C2), 58.0 (CH$_2$O), 106.1 (C1", $^2J_{C-F}$=17 Hz) 115.8 (C6), 120.6 (C7), 126.8 (C8), 133.9 (C4a), 134.1 (C8a), 137.5 (C2" & C6", $J_{C-F}$=254 Hz), 141.7 (C4", $J_{C-F}$=256 Hz), 145.7 (C3" & C5", $J_{C-F}$=254 Hz), 155.1 (C5), 198.2 (C=O) ppm. MS(EI): 342 (M$^+$); MS(ECNI): 161 ([M-PFBz]$^-$, 100%).

4-Pentafluorobenzyloxy-9-fluorenone (15):

Yield: 93%. m.p. 126°–127° C. $^1$H NMR (DMSO-d$_6$), δ: 5.28 (s, 2H, CH$_2$O), 5.13–7.42 (m, 5H, H—C2, H—C3, H—C5, H—C6 & H—C7), 7.60 (d, 2H, J=7.4 Hz, H—C1 & H—C8) ppm; $^{13}$C NMR (DMSO-d$_6$), δ: 57.6 (CH$_2$O), 109.7 (C1', $^2J_{C-F}$=17 Hz), 117.6 (C3), 118.7, 124.0, 128.3, 130.5, 131.9, 133.4, 134.9, 136.0, 137.6 (C2' & C6', $J_{C-F}$=254 Hz), 142.0 (C4', $J_{C-F}$=251 Hz), 145.7 (C3' & C5', $J_{C-F}$=251 Hz), 143.2 (C9a), 193.7 (C=O) ppm. MS(EI): 376 (M$^+$); MS (ECNI): 195 ([M-PFBz]$^-$, 100%).

Similarly, other hydroxy aromatic ketones can also be used for synthesis of the corresponding pentafluorobenzylated ketones by the above procedure.

Synthesis of 3',5'-dimethyl-4'-pentafluorobenzyloxyacetophenone (3):

2,6-Dimethylphenyl pentafluorobenzyl ether:

A mixture of 2,6-dimethylphenol (5 mmol), pentafluorobenzyl bromide (1.3 g, 5 mmol), potassium carbonate (5 g), acetone (30 ml), and 18-crown-6 ether (0.1 g) were stirred under reflux for 5 hours. Work-up procedure was the same as above. Yield: 96%; m.p.: 81°–82° C.; $^1$H NMR, δ: 2.37 (s, 6H, CH$_3$), 4.91 (s, 2H, CH$_2$O), 6.96–7.16 (m, 3H, H—Ar) ppm; $^{13}$C NMR, δ: 15.7 (CH$_3$), 59.9 (CH$_2$O), 110.7 (C2', $^2J_{C-F}$=18 Hz), 124.6 (C4), 129.0 (C3 & C5), 131.1 (C2 & C6), 137.6 (C2' & C6', $J_{C-F}$=253 Hz), 141.7 (C4', $J_{C-F}$=255 Hz), 145.9 (C3' & C5', $J_{C-F}$=250 Hz), 154.6 (C1) ppm.

Friedel-Crafts acetylation of 2,6-dimethylphenyl pentafluorobenzyl ether in the presence of aluminum chloride:

To an ice-cooled, stirred mixture of 2,6-dimethylphenyl pentafluorobenzyl ether (1.34 g, 4.43 mmol), aluminum chloride (0.7 g, 5.2 mmol), and 30 ml of methylene chloride (dried over calcium hydride prior to use), acetyl chloride 0.4 g, 5.1 mmol) was injected slowly. The reaction mixture was then stirred at room temperature overnight. After 30 ml of ice-water was added, the water layer was extracted with ether (3×30 ml). The combined organic layers were washed 30 ml of saturated sodium bicarbonate and 15 ml of water and then was dried over anhydrous magnesium sulfate. After the removal of the solvent, 1.27 g product as white crystal was obtained which consisted of three isomers indicated by GC analysis. PGC separations were done. The spectral data are as follows:

3',5'-Dimethyl-4'-pentafluorobenzyloxyacetophenone (3):

Relative content on GC: 48% (Yield: 40%); m.p. 100°–101° C. $^1$H NMR, δ: 2.36 (s, 6H, CH$_3$Ar), 2.57 (s, 3H, CH$_3$CO), 4.92 (s, 2H, CH$_2$O), 7.67 (s, 2H, H—C2' & H—C6') ppm; $^{13}$C NMR, δ: 16.1 (CH$_3$Ar), 26.5 (CH$_3$CO), 60.1 (CH$_2$O), 110.2 (C1", $^2J_{C-F}$=18 Hz), 129.5 (C2' & C6'), 131.4 (C3' & C5'), 133.6 (C1'), 137.5 (C2" & C6", $J_{C-F}$=258 Hz), 141.8 (C4", $J_{C-F}$=256 Hz), 145.9 (C3" & C5", $J_{C-F}$=250 Hz), 158.7 (C4'), 197.5 (C=O) ppm. MS(EI): 344 (M$^+$); MS(ECNI): 163 ([M-PFBz]$^-$, 100%).

2',6'-Dimethyl-3'-pentafluorobenzylphenyl acetate:

Relative content on GC: 21% (Yield: 17%). $^1$H NMR, δ: 2.12 (s, 3H, CH$_3$—C2'), 2.17 (s, 3H, CH$_3$—C6'), 2.36 (s, 3H, CH$_3$CO), 3.99 (s, 2H, CH$_2$), 6.77 (d, 1H, J=7.8 Hz, H—C4'), 6.98 (d, 1H, J=7.8 Hz, H—C5') ppm; $^{13}$C NMR, δ: 12.3 (CH$_3$—C2'), 16.3 (CH$_3$—C6'), 20.5 (CH$_3$CO), 25.5 (CH$_2$), 113.4 (C1", $^2J_{C-F}$=18 Hz), 125.8 (C4'/C5'), 128.1 (C5'/C4'), 128.4 (C2'/C6'), 128.9 (C6'/C2'), 134.3 (C3'), 137.5 (C2" & C6", $J_{C-F}$=253 Hz), 140.0 (C4", $J_{C-F}$=253 Hz), 145.2 (C3" & C5", $J_{C-F}$=249 Hz), 148.3 (C1'), 168.8 (C=O) ppm. MS(EI): 344 (M$^+$).

2',6'-Dimethyl-4'-pentafluorobenzylphenyl acetate:

Relative content on GC: 31% (Yield: 26%). $^1$H NMR, δ: 2.11 (s, 6H, CH$_3$—Ar), 2.32 (s, 3H, CH$_3$CO), 3.92 (s, 2H, CH$_2$), 6.92 (s, 2H, H—Ar) ppm; $^{13}$C NMR, δ: 16.3 (CH$_3$—Ar), 20.4 (CH$_3$CO), 27.5 (CH$_2$), 114.3 (C1", $^2J_{C-F}$=19 Hz), 128.5 (C3' & C5'), 130.5 (C2' & C6'), 134.8 (C4'), 137.5 (C2" & C6", $J_{C-F}$=252 Hz), 139.9 (C4", $J_{C-F}$252 Hz), 144.9 (C3" & C5", $J_{C-F}$=249 Hz), 147.1 (C1'), 168.9 (C=O) ppm. MS(EI): 344 (M$^+$).

Synthesis of mono- to tetrafluoro-4'-pentafluorobenzyloxyacetophenones (6–9):

Synthesis of 3'-fluoro-4'-pentafluorobenzyloxyacetophenone (6):

1) Synthesis of 2'-fluorophenyl acetate: To a mixture of 2-fluorophenol (5 g, 45 mmol), 50 ml ether, and potassium carbonate (16 g), 5 ml acetic anhydride was added. After stirring under reflux for 3 hours, the reaction mixture was stirred at room temperature overnight. The solid was removed by filtration and washed with ether for several times. The filtrate was then evaporated to remove the solvent and distilled to obtain the product (4.43 g, 64%). $^1$H NMR, δ: 2.32 (s, 3H, CH$_3$), 6.90–7.27 (m, 4H, H—Ar) ppm; $^{13}$C NMR, δ: 20.3 (CH$_3$CO), 116.6 ($^4J_{C-F}$=19 Hz C5'), 123.7 (C4'/C6'), 124.4 ($^3J_{C-F}$=4 Hz, C6'/C4'), 127.0 ($J_{C-F}$=249 Hz, C2'), C3'), 138.1 ($^2J_{C-F}$=13 Hz, C1'), 154.1 ($J_{C-F}$=249 Hz, C2'), 168.3 (C=O) ppm. 2) Synthesis of 3'-fluoro-4'-hydroxyacetophenone: A mixture of 2'-fluorophenyl acetate (1.54 g, 10 mmol) and aluminum chloride (1.70 g, 12.5 mmol) in 10 ml nitrobenzene was stirred at 140°–150° C. for 3 hours. After cooling to room temperature, 15 ml ice-water was added and followed 30 ml of 3N HCl. The water layer was extracted with ether (3×30 ml) and the combined organic layers were washed with concentrated potassium carbonate solution for three times. Then the combined water layers were acidified with 2N HCl. After extraction with ether for several times, the organic layers was dried over anhydrous $MgSO_4$. The removal of ether by evaporation afforded 1.0 g product (65%). It was directly used to next step. 3) Synthesis of 6: A mixture of 3'-fluoro-4'-hydroxyacetophenone (1 g, 6.5 mmol) and pentafluorobenzyl bromide (6.5 mmol), 30 ml acetone, and 5 g potassium carbonate was stirred under reflux for 5 hours. Work-up as usual afforded 1.98 g product (91%). m.p. 99°–100° C. $^1H$ NMR, δ: 2.51 (s, 3H, $CH_3CO$), 5.24 (s, 2H, $CH_2O$), 7.11 ("t", 1H, $J_{5-6}$=8.8 Hz, $^4J_{H-F}$=8.2 Hz, H—C5'), 7.62 (d, 1H, $^3J_{H-F}$=11.2 Hz, H—C2'), 7.70 (d, 1H, $J_{6-5}$=8.8 Hz, H—C6') ppm; $^{13}C$ NMR, δ: 25.9 ($CH_3CO$), 58.5 ($CH_2O$), 109.1 (C1", $^2J_{C-F}$=17 Hz), 114.4 (C5'), 116.0 (C2', $^2J_{C-F}$=19 Hz), 125.4 (C6', $^4J_{C-F}$=3 Hz), 131.7 (C1', $^3J_{C-F}$=5 Hz), 137.4 (C2" & C6", $J_{C-F}$=254 Hz), 141.9 (C4", $J_{C-F}$=256 Hz), 145.7 (C3" & C5", $J_{C-F}$=251 Hz), 149.8 (C4', $^2J_{C-F}$=11 Hz), 152.2 (C3', $J_{C-F}$=249 Hz), 195.5 (C=O) ppm. MS(EI): 334 (M$^+$); MS(ECNI): 153 ([M-PFBz]$^-$, 100%).

Synthesis of 3',5'-Difluoro-4'-pentafluorobenzyloxyacetophenone (7):

1) Synthesis of 2',6'-Difluorophenyl acetate: To a stirred mixture of 2,6-difluorophenol (3.6 g, 27.7 mmol), 30 ml toluene, and 30 ml pyridine, 3 ml of acetyl chloride was added at room temperature. After stirring for 5 hours, 30 ml water was added. The organic layer was separated and evaporated to remove the solvent. The residue was diluted with 40 ml ether and then washed with 30 ml 5% HCl and then 30 ml 5% sodium carbonate. After dried over anhydrous $MgSO_4$, distillation afforded 4.3 g product (90%). $^1H$ NMR, δ: 2.33 (s, 3H, $CH_3CO$), 6.94 (t, 2H, $J_{H-F}$=$J_{H-H}$=7.9 Hz, H—C3 & H—C5), 7.12 (m, 1H, H—C4) ppm; 13C NMR, δ: 19.5 ($CH_3CO$), 111.9 (C3 & C5, $^2J_{C-F}$=22 Hz, $^4J_{C-F}$=6 Hz), 126.3 (C4, $^3J_{C-F}$=9 Hz), 155.2 (C2 & C6, $J_{C-F}$=250 Hz, $^3J_{C-F}$=4 Hz), 167.2 (C=O) ppm. IR (film): $v_{max}$: 3010 (w), 1730 (vs, C=O), 1565 (m), 1440 (s), 1335 (m), 1255 (s), 1210 (m), 1120 (vs, C—O), 1010 (m), 965 (s), 860 (s), 740 (s), 710 (m), 670 (w) cm$^{-1}$. 2) Synthesis of 3',5'-difluoro-4'-hydroxyacetophenone: A mixture of 2',6'-difluorophenyl acetate (4.2 g, 24.4 mmol) and aluminum chloride (6.0 g, 4.5 mmol) in 100 ml of nitrobenzene was stirred at 140° to 150° C. for 5 hours. Work-up procedure was the same as synthesis of 3'-fluoro-4'-hydroxyacetophenone. 2.2 g product was obtained (52%). $^1H$ NMR, δ: 2.32 (s, 1H, OH), 2.57 (s, 3H, $CH_3$), 7.53 (d, 2H, J=8.1 Hz, HC2' & HC6') ppm; $^{23}C$ NMR, δ: 25.4 ($CH_3$), 111.8 ($^2J_{C-F}$=22 Hz, $^4J_{C-F}$8 Hz, C2' & C6'), 117.8 ($^3J_{C-F}$=9 Hz, C1'), 139.1 ($^2J_{C-F}$=16 Hz, C4), 151.6 ($J_{C-F}$245 Hz, $^3J_{C-F}$=7 Hz, C3' & C5'), 196.0 (C=O) ppm. 3) Synthesis of 7: A mixture of 3',5'-difluoro-4'-hydroxy-acephenone (2.2 g, 12.8 mmol), pentafluoro-benzyl bromide (12.8 mmol), 30 ml of acetone, and 5 g potassium carbonate was stirred under reflux for 5 hours. Work-up procedure was as usual. 4 g product was obtained (88%). $^1H$ NMR, δ: 2.58 (s, 3H, $CH_3CO$), 5.38 (s, 2H, $CH_2O$), 7.52 (d, 2H, $^3J_{H-F}$=8.7 Hz, H—C2' & HC6') ppm; $^{13}C$ NMR, δ: 25.8 ($CH_3CO$), 62.3 ($CH_2O$), 109.5 (C1", $^2J_{C-F}$=17 Hz), 112.3 (C2' & C6', $^2J_{C-F}$=24 Hz, $^4J_{C-F}$=8 Hz), 132.8 (C1", $J_{C-F}$7 Hz), 137.4 (C2" & C6", $J_{C-F}$=252 Hz), 138.2 (C4', $^3J_{C-F}$=15 Hz), 142.0 (C4", $J_{C-F}$=256 Hz), 145.8 (C3" & C5", $J_{C-F}$=253 Hz), 155.5 (C3' & C5', $J_{C-F}$=251 Hz, $^3J_{C-F}$=5 Hz), 194.4 (C=O)ppm. MS(EI): 352 (M$^+$); MS(ECNI): 171 ([M-PFBz]$^-$, 100%).

Synthesis of 4'-pentafluorobenzyloxy-2',3',5'-trifluoroacetophenone (8):

A mixture of 2',3',4',5'-tetrafluoroacetophenone (0.96 g, 5 mmol), pentafluorobenzyl alcohol (1.0 g, 5 mmol), potassium carbonate (7 g), toluene (30 ml), and 18-crown-6 ether (0.1 g) were stirred under reflux for 8 hours. After cooling to room temperature and addition of some Celite 521, the reaction mixture was filtered and the residue was washed with ether three times. Then the filtrate was evaporated on a rotavapor. The crude products were separated by PGC with column A. 1.31 g product was obtained. (71%). m.p.: 76°–77° C. $^1H$ NMR, δ: 2.65 (d, 3H, $^5J_{H-F}$=5.2 Hz, $CH_3$—CO), 5.42 (s, 2H, $CH_2O$), 7.46 (ddd, 1H, $^2J_{H-F}$=11.3 Hz, $^3J_{H-F}$=6.1 Hz, $^4J_{H-F}$=2.4 Hz, H—C6') ppm; $^{13}C$ NMR, δ: 31.1 ($CH_3CO$, $^4J_{C-F}$=8 Hz), 62.6 ($CH_2O$), 109.1 (C1", $^2J_{C-F}$=19 Hz), 111.1 (C6', $^2J_{C-F}$=21 Hz, $^3J_{C-F}$=3 Hz), 121.0 (C1'), 137.5 (C2" & C6", $J_{C-F}$=250 Hz), 142.2 (C4", $J_{C-F}$=249 Hz), 144.6 (C3', $J_{C-F}$=253 Hz, $^2J_{C-F}$=17 Hz, $^3J_{C-F}$=5 Hz), 145.8 (C3" & C5", $J_{C-F}$=251 Hz), 148.2 (C2', $J_{C-F}$=254 Hz, $^2J_{C-F}$=13 Hz, $^4J_{C-F}$=3 Hz), 151.0 (C5', $J_{C-F}$=248 Hz, $^3J_{C-F}$=$^4J_{C-F}$=3 Hz), 168.4 (C4'), 192.4 (C=O) ppm. MS(EI): 370 (M$^+$) MS(ECNI): 189 ([M-PFBz]$^-$, 100%).

Synthesis of 4'-pentafluorobenzyloxy-2',3',5'6'-tetrafluoroacetophenone (9):

A mixture of pentafluoroacetophenone (1.05 g, 5 mmol), pentafluorobenzyl alcohol (1.0 g, 5 mmol), potassium carbonate (7 g), toluene (30 ml), and 18-crown-6 ether (0.1 g) were stirred under reflux for 8 hours. Work-up procedure was the same as synthesis of 8. 0.89 g product was obtained (46%). $^1H$ NMR, δ: 2.62 (t, 3H, $^5J_{H-F}$=2.0 Hz, $CH_3CO$), 5.41 (s, 2H, $CH_2O$) ppm; $^{13}C$ NMR, δ: 32.3 ($CH_3CO$), 63.0 ($CH_2O$), 108.9 (C1", $^2J_{C-F}$=17 Hz), 114.4 (C1' $^2J_{C-F}$=16 Hz), 137.5 (C2" & C6", $J_{C-F}$=258 Hz), 138.6 (C4'), 141.2 (C3' & C5' $J_{C-F}$=249 Hz), 142.4 (C4", $J_{C-F}$=257 Hz), 144.8 (C2' & C6', $J_{C-F}$=263 Hz), 145.8 (C3" & C5", $J_{C-F}$=252 Hz), 195.5 (C=O) ppm. MS(EI): 388 (M$^+$); MS(ECNI): 207 ([M-PFBz]$^-$, 100%). Besides 9, 0 31 g 2'-pentafluorobenzyloxy-3',4',5',6'-tetrafluoroacetophenone was also obtained by PGC separation: $^1H$ NMR, δ: 2.51 (d, 3H, $^5J_{H-F}$=1.6 Hz, $CH_3CO$), 5.25 ("s", 2H with fine splitting, $CH_2O$) ppm; $^{13}C$ NMR, δ: 32.3 ($CH_3CO$), 63.7 ($CH_2O$), 108.9 (C1", $^2J_{C-F}$=18 Hz), 120.9 (C1'), 137.5 (C2" & C6", $J_{C-F}$=253 Hz), 137.7 (C4' & C5', $J_{C-F}$=253 Hz), 138.2 (C2'), 142.1 (C4", $J_{C-F}$=252 Hz), 142.2 (C3'/C6', $J_{C-F}$=252 Hz), 143.8 (C6'/C3', $J_{C-F}$=254 Hz), 145.8 (C3" & C5", $J_{C-F}$=259 Hz), 194.0 (C=O) ppm.

General procedure for synthesis of compounds 10–12:

A mixture of 3',5'-dihydroxyacetophenone (5 mmol), pentafluoro-benzyl bromide (5 mmol), ethyl bromide or methyl-$d_6$ iodide (5 mmol), 15 ml of acetone, and 0.1 g 18-crown-6 ether was stirred at room temperature for 16 hours. After addition of 2 g of Celite 521, the reaction mixture was filtered and the residue was washed with acetone three times. Then the filtrate was evaporated on a rotavapor. The crude products were separated by PGC. The yields and m.p. and the spectral data are as follows:

3'-Ethoxy-5'-pentafluorobenzyloxyacetophenone (10):

Yield: 33%. m.p. 66°–67° C. $^1H$ NMR, δ: 1.43 (t, 3H, J=7.0 Hz, $CH_3$), 2.58 (s, 3H, $CH_3CO$), 4.06 (q, 2H, J=7.0 Hz, $CH_2Me$), 5.15 (s, 2H, $CH_2Ar$), 6.70 (t, 1H, J=2.3 Hz, H—C4'), 7.15 (m, 2H, $J_{2-4/6-4}$=2.3 Hz, $J_{2-6/6-2}$=1.5 Hz, H—C2' & H—C6') ppm; $^{13}C$ NMR, δ: 14.6 ($CH_3$), 26.6 ($CH$—$_3CO$), 57.6 ($CH_2Ar$), 63.9 ($CH_2Me$), 106.2 (C4'), 106.4 (C6'), 108.1 (C2'), 109.1 (C1", $^2J_{C-F}$=18 Hz), 137.6

(C2" & C6", $J_{C-F}$=256 Hz), 139.1 (C1'), 141.8 (C4", $J_{C-F}$=256 Hz), 147.7 (C3" & C5", $J_{C-F}$=254 Hz), 159.1 (C3'), 160.3 (C5'), 197.5 (C=O) ppm. MS(EI): 360 (M$^+$); MS(ECNI): 179 ([M-PFBz]$^-$, 100%).

3'-(Methoxy-$d_6$)-5'-pentafluorobenzyloxyacephone (11):

Yield: 30%. m.p. 67°–68° C. $^1$H NMR, δ: 2.59 (s, 3H, CH$_3$CO), 5.16 (s, 2H, CH$_2$O), 6.71 ("t", 1H, J=2.3 Hz, H—C4'), 7.14–7.19 (m, 2H, H—C2' & H—C6') ppm; $^{13}$C NMR, δ: 26.7 (CH$_3$CO), 57.6 (CH$_2$Ar), 70.3 (CD$_3$), 106.0 (C4'), 106.4 (c6'), 107.5 (C2'), 109.7 (C1", $^2J_{C-F}$=17 Hz), 137.5 (C2" & C6", $J_{C-F}$=250 Hz), 139.1 (C1'), 141.7 (C4", $J_{C-F}$=242 Hz), 145.7 (C3" & C5", $J_{C-F}$=251 Hz), 159.1 (C3'), 160.9 (C5'), 195.5 (C=O) ppm. MS(EI): 349(M$^+$); MS(ECNI): 168 ([M-PFBz]$^-$, 100%).

3',5'-Di[(pentafluorobenzyl)oxy]acetophenone (12):

Synthesized by 1:2 ratio of 3',5'-dihydroxyacetophenone to pentafluorobenzyl bromide. Yield: 98%. m.p. 102°–103° C. $^1$H NMR, δ: 2.60 (s, 3H, CH$_3$CO), 5.22 (s, 4H, CH$_2$O), 6.83 (bs, 1H, H—C4'), 7.24 (d, 2H, J=1.8 Hz, H—C2' & H—C6') ppm; $^{13}$C NMR, δ: 26.0 (CH$_3$CO), 57.4 (CH$_2$O), 106.4 (C4'), 107.4 (C2' & C6'), 109.7 (C1", $^2J_{C-F}$=17 Hz), 137.4 (C2" & C6", $J_{C-F}$=249 Hz), 139.2 (C1'), 141.7 (C4", $J_{C-F}$=256 Hz), 145.7 (C3" & C5", $J_{C-F}$=251 Hz), 159.2 (C3' & C5'), 196.7 (C=O) ppm. MS(EI): 331 ([M-PFBz]$^+$); MS(ECNI): 331 ([M-PFBz]$^-$, 100%).

Synthesis of 4'-(4"-methoxy-2",3",5",6"-tetrafluorobenzyl)oxyacetophenone (16):

A mixture of 1 (0.63 g, 2 mmol), 30 ml of methanol, and 0.2 g of sodium methoxide was stirred under reflux overnight. After the removal of most of methanol by distillation, 15 ml 3% HCl was added. The reaction mixture was extracted with ether and washed with water. After the evaporation to remove the solvent, the crude product was recrystalized from hexane. 0.59 g product was obtained (90%). m.p. 104°–105° C. $^1$H NMR, δ: 2.57 (s, 3H, CH$_3$CO), 4.11 (t, 3H, $^5J_{H-F}$=1.5 Hz, CH$_3$O), 5.17 (s, 2H, CH$_2$O), 7.01 (d, 2H, J=8.8 Hz, H—C3' & H—C5'), 7.96 (d, 2H, J=8.8 Hz, H—C2' & H—C6') ppm; $^{13}$C NMR, δ: 26.3 (CH$_3$), 57.5 (CH$_2$O), 61.8 (CH$_3$O, $^5J_{C-F}$=4 Hz), 107.3 (C1", $^2J_{C-F}$=18 Hz), 114.3 (C3' & C5'), 130.6 (C2' & C6'), 131.0 (C1'), 139.5 (C4"), 140.7 (C2" & C6", $J_{C-F}$=249 Hz), 145.9 (C3" & C5", $J_{C-F}$=249 Hz), 161.7 (C4'), 196.4 (C=O) ppm. MS(EI): 328(M$^+$); MS(ECNI): 135 ([M-PFBz]$^-$, 100%).

(2) Synthesis of ketones with Q=—CH$_2$N(COR)—:

This series of ketones can be synthesized by reaction of the corresponding amino substituted aromatic ketones with pentafluorobenzyl bromide in the presence of potassium carbonate and then the reactions with the corresponding acid chlorides. For example, the reaction of 4'-amino-acetophenone with pentafluorobenzyl bromide can afford 4'-pentafluoro-benzylaminoacetophenone as the main product. The further reaction with sodium hydride and then acetyl chloride can give N-acetyl-4'-pentafluoro-benzylaminoacetophenone.

Similarly, these ketones can be prepared directly from the N-penta-fluorobenzylation of the corresponding acetyl aromatic amides. For example, the reaction of pentafluorobenzyl bromide with the intermediate obtained from the reaction of N,4-diacetylaniline with sodium hydride can afford the same product as above.

(3) Synthesis of ketones with Q=—CONH—:

This series of ketones can be synthesized by the reaction of the corresponding amino substituted aromatic ketones with pentafluorobenzoyl chloride or its derivatives. For example, the reaction of 4'-aminoaceto-phenone with pentafluorobenzoyl chloride can afford 4'-pentafluoro-benzoylaminoacetophenone as the product.

(4) Synthesis of ketones with Q=—CONR—:

This series of ketones can be synthesized by derivatization of the ketones in Series (3). For example, the reactions of alkyl bromides or iodides with the intermediate formed from the reaction of 4'-pentafluoro-benzoylaminoacetophenone with sodium hydride can afford a group of N-alkylated products.

(5) Synthesis of ketones with Q=—CON(COR)—:

Similar to the synthesis of ketones in Series (4), this series of ketones can also be obtained from the ketones in Series (3). For example, the reaction of aliphatic or aromatic acid chlorides with the intermediate formed from the reaction of 4'-pentafluorobenzoylamino-acetophenone with sodium hydride can afford a group of N-acylated products.

(6) Synthesis of ketones with Q=—CH$_2$OAr—:

For the synthesis of the ketones where Ar is phenylene, a Friedel-Crafts pentafluorobenzylation can be used to give the corresponding acetyl substituted biphenyl derivatives. For example, the reaction of pentafluoro-benzyl bromide with 4-acetylbiphenyl can afford 4-acetyl-4'-pentafluoro-benzylbiphenyl as the main product.

If Ar is phenyleneoxy, then the reaction of hydroxy substituted acetyl diphenyl ether derivatives can be used. For example, the reaction of 4-acetylphenyl 4'-hydroxyphenyl ether with pentafluorobenzyl bromide under the Series (1) reaction conditions can afford 4-acetylphenyl 4'-pentafluorobenzyloxyphenyl ether as the product.

When Ar is benzyleneoxy, the reaction of hydroxy aromatic ketones with 4'-(pentafluorobenzyloxy)benzyl bromide can be used. The reaction conditions can be similar to the reactions in synthesis of Series (1). The latter bromide can be made from the bromination of 4'-(pentafluoro-benzyloxy)toluene by using N-bromosuccinimide (NBS) or bromine/hv as reagents.

When Ar is a polyfluoronated aromatic ring, a direct pentafluoro-benzyloxylation can be carried out by using pentafluorobenzyl alcohol as a nucleophile to replace a fluorine atom on the ring. For example, all of those ketones containing a pentafluorophenyl group can react with pentafluorobenzyl alcohol in the presence of potassium carbonate under reflux of toluene or in DMF at 150° C. overnight. The corresponding 4"-penta-fluorobenzyloxy-4'-(2",3",5",6"-tetrafluorobenzyl)oxy substituted aceto-phenones can be obtained as the main products.

(7) Synthesis of ketones with Q=—CONHAr—:

For the synthesis of the ketones where Ar is phenylene, a pentafluorobenzoylation can be done to give the corresponding acetyl substituted aminobiphenyl derivatives. For example, the reaction of pentafluoro-benzoyl chloride with 4-acetyl-4'-aminobiphenyl can afford 4-acetyl-4'-(N-pentafluorobenzoyl)aminobiphenyl as the product.

If Ar is phenyleneoxy, then the reactions of amino substituted acetyl diphenyl ether derivatives can be used. For example, the reaction of 4-acetylphenyl 4'-aminophenyl ether with pentafluorobenzoyl chloride can afford 4-acetylphenyl 4'-(N-pentafluorobenzoyl)aminophenyl ether as the product.

When Ar is benzyleneoxy, the reactions of hydroxy aromatic ketones with 4'-(N-pentafluorobenzoyl)aminobenzyl bromide can be used. The reaction conditions can be similar to the reactions in synthesis of Series (1). The latter bromide can be made from the bromination of 4-methyl-N-pentafluorobenzoylaniline by using NBS or bromine/hv as reagents.

EXAMPLE II

Olefin, glycol, and α-hydroxyketo release tags corresponding to the ketone Sg group precursors of Example I can include the following compounds. When the release tags are synthesized from ester precursors, the corresponding acid release tag is produced by e.g., hydrolyzing the ester with 1.1 molar equivalent of NaOH in 50% aqueous methanol at room temperature for 1 hour.

Olefins 17a–32a

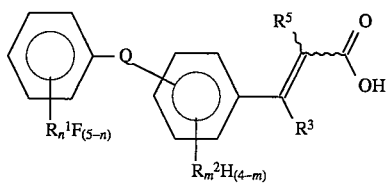

| No. | $R^1$ | $R^2$ | $R^3$ | Q | $R^5$ |
|---|---|---|---|---|---|
| 17a | / | / | $CH_3$ | 4'-$CH_2O$ | H |
| 18a | / | 3'-$CH_3$ | $CH_3$ | 4'-$CH_2O$ | H |
| 19a | / | 3'-$CH_3$ 5'-$CH_3$ | $CH_3$ | 4'-$CH_2O$ | H H |
| 20a | / | 3'-$OCH_3$ | $CH_3$ | 4'-$CH_2O$ | H |
| 21a | / | 3'-$OCH_3$ 5'-$OCH_3$ | $CH_3$ | 4'-$CH_2O$ | H H |
| 22a | / | 3'-F | $CH_3$ | 4'-$CH_2O$ | H |
| 23a | / | 3'-F 5'-F | $CH_3$ | 4'-$CH_2O$ | H H |
| 24a | / | 2'-F 3'-F 5'-F | $CH_3$ | 4'-$CH_2O$ | H H H |
| 25a | / | 2'-F 3'-F 5'-F 6'-F | $CH_3$ | 4'-$CH_2O$ | H H H H |
| 26a | / | 3'-$OC_2H_5$ | $CH_3$ | 5'-$CH_2O$ | H |
| 27a | / | 3'-$OCD_3$ | $CH_3$ | 5'-$CH_2O$ | H |
| 28a | / | 3'-$OCH_2C_6F_5$ | $CH_3$ | 5'-$CH_2O$ | H |
| 29a | / | / | $C_2H_5$ | 4'-$CH_2O$ | H |
| 30a | / | $CH_2CH_2CH_2$* | | 5'-$CH_2O$ | H |
| 31a | / | o-Phenylene* | | 4'-$CH_2O$ | H |
| 32a | $OCH_3$ | / | $CH_3$ | 4'-$CH_2O$ | H |

*$R^2$, $R^3$

General procedure for synthesis of the ester precursor olefins 17, 18, 20, and 32:

The reactions were carried out under nitrogen. To sodium hydride (0.13 g, 5.4 mmol) suspended in 30 ml of anhydrous THF, methyl diethylphosphono acetate (1.13 g, 5.4 mmol) was injected slowly. After stirring for 15 min, the corresponding ketone (1, 2, 4, or 16, 5 mmol) in 15 ml of anhydrous THF was added dropwise. The reaction mixture was stirred under reflux for another 10 hours. After cooling to room temperature, 15 ml water was added and water layer was extracted with ether. The organic layer was dried over anhydrous $MgSO_4$. After the removal of the solvent, the crude product was purified by silica flash column chromatography (hexane:ethyl acetate=5:1). The data is listed as follows:

Methyl 3-[4'-(pentafluorobenzyloxy)phenyl]crotonate (17):

Yield: 68%. E:Z ratio=6:1. E-isomer: $^1H$ NMR, δ: 2.56 (d, 3H, $^4J$=0.6 Hz, $CH_3$), 3.74 (s, 3H, $CH_3O$), 5.15 (s, 2H, $CH_2O$), 6.11 (q, 1H, $^4J$=0.6 Hz, H—C2), 6.97 (d, 2H, J=8.8 Hz, H—C3' & H—C5'), 7.46 (d, 2H, J=8.8 Hz, H—C2' & H—C6') ppm.

Methyl 3-[3'-methyl-4'-(pentafluorobenzyloxy) phenyl]crotonate (18):

Yield: 65%. E:Z ratio=6:1. E-isomer: $^1H$ NMR, δ: 2.56 (d, 3H, 2.19 (s, 3H, $CH_3$—C3'), 2.55 (d, 3H, $^4J$=1 Hz, $CH_3$—C3), 3.73 (s, 3H, $CH_3O$), 5.13 (s, 2H, $CH_2O$), 6.09 (q, 1H, $^4J$=1 Hz, H—C2), 6.93 (d, 1H, J=8.4 Hz, H—C5'), 7.30 (bs, 1H, H—C2'), 7.32 (d, 1H, J=8.4 Hz, H—C6') ppm.

Methyl 3-[3'-methoxy-4'-(pentafluorobenzyloxy)phenyl] crotonate (20):

Yield: 56%. E:Z ratio=6:1. E-isomer: $^1H$ NMR, δ: 2.57 (bs, 3H, $CH_3$), 3.75 (s, 3H, $CH_3O$), 3.88 (s, 3H, $CH_3$—C3'), 5.18 (s, 2H, $CH_2O$), 6.11 (bs, 1H, H—C2), 6.97 (dd, 1H, $J_{5'-6'}$=8.3 Hz, $J_{5'-2'}$=3.6 Hz, H—C5'), 7.03 (bs, 1H, H—C2'), 7.06 (dd, 1H, $J_{6'-5}$=8.3 Hz, $J_{6'-2}$=2.1 Hz, H—C6') ppm.

Methyl 3-[4'-(4"-methoxy-2",3",5",6"-tetrafluorobenzyloxy)phenyl]crotonate (32):

Yield: 58%. E:Z ratio=6:1. E-isomer: $^1H$ NMR, δ: 2.57 (d, 3H, $^4J$=0.6 Hz, $CH_3$—C3), 3.75 (s, 3H, $CH_3O$), 4.01 (t, 3H, $^5J_{H-F}$=1.4 Hz, $CH_3O$—C4"), 5.15 (s, 2H, $CH_2O$), 6.11 (q, 1H, $^4J$=0.6 Hz, H—C2), 6.97 (d, 2H, J=8.8 Hz, H—C3' & H—C5'), 7.46 (d, 2H, J=8.8 Hz, H—C2'& H—C6') ppm.

Other olefins (19, 21–31) can be synthesized by the same procedure as the above.

Glycols 33–48

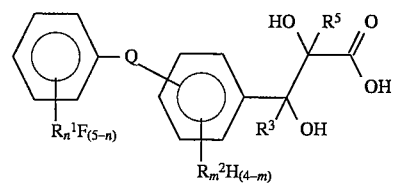

| No. | $R^1$ | $R_2$ | $R^3$ | Q | $R^5$ |
|---|---|---|---|---|---|
| 33 | / | / | $CH_3$ | 4'-$CH_2O$ | H |
| 34 | / | 3'-$CH_3$ | $CH_3$ | 4'-$CH_2O$ | H |
| 35 | / | 3'-$CH_3$ 5'-$CH_3$ | $CH_3$ | 4'-$CH_2O$ | H H |
| 36 | / | 3'-$OCH_3$ | $CH_3$ | 4'-$CH_2O$ | H |
| 37 | / | 3'-$OCH_3$ 5'-$OCH_3$ | $CH_3$ | 4'-$CH_2O$ | H H |
| 38 | / | 3'-F | $CH_3$ | 4'-$CH_2O$ | H |
| 39 | / | 3'-F 5'-F | $CH_3$ | 4'-$CH_2O$ | H H |
| 40 | / | 2'-F 3'-F 5'-F | $CH_3$ | 4'-$CH_2O$ | H H H |
| 41 | / | 2'-F 3'-F 5'-F 6'-F | $CH_3$ | 4'-$CH_2O$ | H H H H |
| 42 | / | 3'-$OC_2H_5$ | $CH_3$ | 5'-$CH_2O$ | H |
| 43 | / | 3'-$OCD_3$ | $CH_3$ | 5'-$CH_2O$ | H |
| 44 | / | 3'-$OCH_2C_6F_5$ | $CH_3$ | 5'-$CH_2O$ | H |
| 45 | / | / | $C_2H_5$ | 4'-$CH_2O$ | H |
| 46 | / | $CH_2CH_2CH_2$ | | 5'-$CH_2O$ | H |
| 47 | / | o-Phenylene | | 4'-$CH_2O$ | H |
| 48 | $OCH_3$ | / | $CH_3$ | 4'-$CH_2O$ | H |

Synthesis of 3-(3'-methyl-4'-pentafluorobenzyloxy)phenyl-2,3-dihydroxybutanoic acid (34):

To a stirred mixture of 100 mg (394 μmol) of osmium tetroxide in 10 ml of anhydrous tetrahydrofuran and 2 ml of pyridine under nitrogen, 100 mg (259 μmol) of olefin ester 18 in 2 ml of tetrahydrofuran was injected. The reaction mixture was stirred at room temperature for 3 hours. After 10 ml of 10% sodium sulfite solution was added, stirring was continued for 1.5 hours. The reaction mixture was extracted with ether (4×20 ml) and the combined organic layer was dried over magnesium sulfate. After the solvent was evaporated, 105 mg (96%) of the crude product was obtained as yellowish oil (TLC showed one spot, hexane:ethyl acetate= 5:1), which was hydrolyzed to the product.

General Procedure for Synthesis of Glycols (33–48) from Ketones (1–16) or Olefins (17–32):

Method 1:

The synthesis directly from the reactions of the corresponding ketones with tris(trimethylsilyloxy)ethylene can be performed. For example, the reaction with 1–16 can be carried out in anhydrous methylene chloride at room temperature for 8 hours and tin tetrachloride (Wissner, A.; *Synthesis*, 1979, 27) or trimethylsilyl trifluoromethanesulfonate (Oesterle, T.; Simchen, G.; *Liebigs Ann. Chem.*, 1987, 693) can be used as catalyst. The hydrolysis of the formed trimethylsilylated intermediates by using acetic acid/THF/water=2:2:1 can afford the corresponding crude glycols in good yields. Then chromatographic separations can provide pure glycols.

Method 2:

The synthesis from the olefins can be performed as follows: the reaction of the corresponding olefins (17–32) with osmium tetroxide/pyridine can be carried out in anhydrous THF under nitrogen at room temperature for several hours. After the treatment with 10% sodium bisulfite, workup will afford the corresponding glycol methyl esters. Then the hydrolysis of the esters with aqueous sodium hydroxide in methanol will afford the products.

α-Hydroxyketos as the α-hydroxyacids 49–64

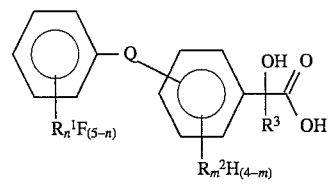

| No. | $R^1$ | $R^2$ | $R^3$ | Q |
|---|---|---|---|---|
| 49 | / | / | $CH_3$ | 4'-$CH_2O$ |
| 50 | / | 3'-$CH_3$ | $CH_3$ | 4'-$CH_2O$ |
| 51 | / | 3'-$CH_3$ 5'-$CH_3$ | $CH_3$ | 4'-$CH_2O$ |
| 52 | / | 3'-$OCH_3$ | $CH_3$ | 4'-$CH_2O$ |
| 53 | / | 3'-$OCH_3$ 5'-$OCH_3$ | $CH_3$ | 4'-$CH_2O$ |
| 54 | / | 3'-F | $CH_3$ | 4'-$CH_2O$ |
| 55 | / | 3'-F 5'-F | $CH_3$ | 4'-$CH_2O$ |
| 56 | / | 2'-F 3'-F 5'-F | $CH_3$ | 4'-$CH_2O$ |
| 57 | / | 2'-F 3'-F 5'-F 6'-F | $CH_3$ | 4'-$CH_2O$ |
| 58 | / | 3'-$OC_2H_5$ | $CH_3$ | 5'-$CH_2O$ |
| 59 | / | 3'-$OCD_3$ | $CH_3$ | 5'-$CH_2O$ |
| 60 | / | 3'-$OCH_2C_6F_5$ | $CH_3$ | 5'-$CH_2O$ |
| 61 | / | / | $C_2H_5$ | 4'-$CH_2O$ |
| 62 | / | $CH_2CH_2CH_2$* | | 5'-$CH_2O$ |
| 63 | / | o-Phenylene* | | 4'-$CH_2O$ |
| 64 | $OCH_3$ | / | $CH_3$ | 4'-$CH_2O$ |

*$R^2$, $R^3$

Synthesis of α-Hydroxy acids 49–64:

This series of acids can be synthesized by the hydrolysis of the corresponding substituted α-hydroxynitriles, which can be obtained in turn from the reaction of corresponding aromatic ketones 1–16 with trimethylsilyl cyanide (Croutas, W. C.; Felker, D.; *Synthesis*, 1980, 861). For example, the reaction of 1 with n=0 with trimethylsilyl cyanide in the presence of zinc iodide in anhydrous ether can afford 2-hydroxy-2-(4'-pentafluorobenzyloxy)-phenylpropionitrile. The hydrolysis of the cyano group to a carboxylic group under basic or acidic conditions can produce the corresponding α-hydroxy acid 49.

EXAMPLE III

Other examples of ketones useful as Sg precursors and their corresponding olefin, glycol, and α-hydroxyketo release tags are given below.

Ketones 65

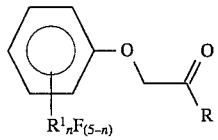

wherein $R^1$=H, $CF_3$, R, or OR;

n=0 to 2; and

R=C1 to C8 alkyl, benzyl, or phenyl which can contain one or more of H, D, or F.

Synthesis of Pentafluorophenoxy acetone (65 with n=0):

To 15 ml acetone, 2.54 g (10 mmol) iodine was added and then stirred for two hours at room temperature. The reaction mixture was added dropwise into a stirred mixture of 0.92 g (5 mmol) pentafluorophenol, 5 g potassium carbonate, 0.1 g triethylbenzylammonium chloride (TEBA), and 30 ml acetone. After refluxing for 3 hours, the inorganic substances were removed by filtration. The solvent was evaporated, the residue was dissolved in 30 ml of pentane, and 3 g silica gel was added for decolorization. Preparative GC using a 10×¼" 20% SE-30 on Chromosorb W (60–80 mesh) column gave 0.28 g (23%) of product.

Similarly, other ketones 65 can be prepared by reaction of $R^1$ substituted tetrafluorophenol or $(R^1)_2$ substituted trifluorophenol with α-iodoacetone in the presence of potassium carbonate.

Olefins 66

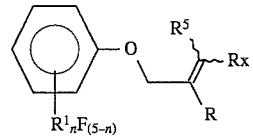

wherein $R^1$=H, $CF_3$, R or OR;

$R^5$=H or R;

n=0 to 2;

R=C1 to C8 alkyl, benzyl, or phenyl which can contain one or more of H, D, or F;

Rx=reactivity group.

Synthesis of olefins 66 with Rx=COOH:

Method 1:

The olefins 66 can be synthesized from the ketones 65 in the same way that the olefins release tags 17a–32a were synthesized from ketones 1–16.

Method 2:

The olefins 66 can also be prepared by reacting the corresponding substituted phenols with ethyl 4-bromo-3-methyl-2-butenate in the presence of potassium carbonate and small amount of 18-crown-ether in methylene chloride. The starting material ethyl 4-bromo-3-methylbutenate has been obtained from the reaction of ethyl 3,3-dimethylacrylate with N-bromosuccinimide (NBS) as follows: to 20 g of ethyl 3,3-dimethylacrylate in 250 ml of carbon tetrachloride, 30 g of N-bromosuccinimide (NBS) and 0.01 g of azobisisobutyronitrile were added. The mixture was refluxed for 3 hours. Succinimide was removed by filtration and the filtrate was washed with chloroform. The combined organic layers were washed sequentially with saturated sodium sulfite, saturated sodium chloride and then dried over anhydrous magnesium sulfate. Evaporation of the solvent afforded 34.4 g ethyl 4-bromo-3-methyl-2-butenate (Safaryn, J. E.; Chiarello, J.; Chen, K. M.; Joullie, M. M.; *Tetrahedron*, 1986, 42, 2635). The product can be further purified by silica gel flash column chromatography using ether/hexane (e.g. 1:50) as eluent, and hydrolyzed to the corresponding carboxylic acid with aqueous methanolic NaOH.

Glycols 67

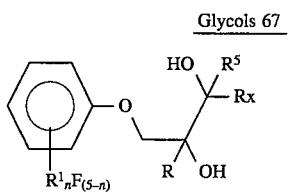

wherein $R^1$=H, $CF_3$, R or OR;

$R^5$=H or R;

n=0–2;

R=C1 to C8 alkyl, benzyl, or phenyl which can contain one or more H, D, or F; and Rx=reactivity group.

Synthesis of Glycols 67 with Rx=COOH:

Method 1:

The glycols 67 can be synthesized from ketones 65 in the same way that glycol release tags 33–48 were synthesized from ketones 1–16.

Method 2:

The glycols 67 can also be synthesized from olefins 66 in the same way that glycol release tags 33–48 were prepared from olefin esters 17–32.

α-Hydroxyketos 68

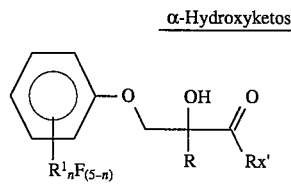

wherein $R^1$=H, $CF_3$, R, or OR;

n0–2;

R=C1 to C8 alkyl, benzyl, or phenyl which can contain one or more H, D, or F; and CORX'=reactivity group.

Synthesis of α-hydroxyketos 68:

This series of compounds with CORx'=COOH can be prepared from the hydrolysis of the corresponding esters of 2-methyl-2-hydroxy-3-polyfluorophenoxypropionic acids, which can be synthesized from the reaction of the epoxides of α-alkyl acrylic acid esters with hydroxy substituted polyfluorinated phenyl compounds in the presence of bases. For example, the reaction of the epoxide of methyl methacrylate with pentafluorophenol in acetone in the presence of excess of potassium carbonate can afford methyl 2-hydroxy-2-methyl-3-pentafluorophenoxypropionate. Then the hydroxy acids can be made from the hydrolysis of the above ester by using a methanol solution of sodium hydroxide.

Ketones 69

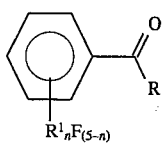

wherein $R^1$=H, $CF_3$, R, or OR;

n=0–2; and

R=C1 to C8 alkyl, benzyl, or phenyl which can contain one or more H, D, or F.

Synthesis of ketones 69:

This series of ketones can be synthesized from the acid chloride with the corresponding organic zinc compounds which made from the reactions of zinc with the alkyl and aryl iodides or bromides under ultrosonication. For example, the reaction of pentafluorobenzoyl chloride with difluorohexyl zinc which can be made from the reaction of perfluorohexyl iodide with zinc dust in THF under ultrasonication can afford perfluoro-1-phenylheptanone as the product. Similarly, the reaction of pentafluorobenzoyl chloride with dipentafluorobenzyl zinc which can be made from the reaction of pentafluorobenzyl bromide with zinc dust in THF under ultrasonication can afford 1,2-dipentafluorophenylethanone as the product.

Olefins 70

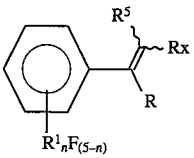

wherein $R^1$=H, $CF_3$, R, or OR;

$R^5$=H or R;

n=0–2;

R=C1 to C8 alkyl, benzyl, or phenyl which can contain one or more H, D, or F; and Rx=reactivity group.

Synthesis of Olefins 70 with Rx=COOH:

Olefins 70 with Rx=COOH can be synthesized from ketones 69 in the same way that olefins 17a–32a can be or were synthesized from ketones 1–16.

Glycols 71

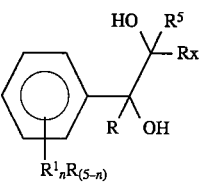

wherein $R^1$=H, $CF_3$, R, or OR;

$R^5$=H or R;

n=0–2;

R=C1 to C8 alkyl, benzyl, or phenyl which can contain one or more H, D, or F; and Rx=reactivity group.

Synthesis of Glycols 71 with Rx=COOH:

Glycols 71 with Rx=COOH can be synthesized from olefins 70 in the same way that glycols 33–48 can be or were synthesized from olefins 17–32.

α-Hydroxyketos 72

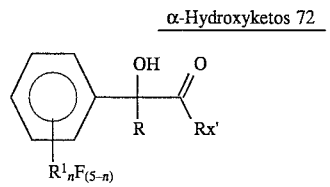

wherein $R^1$=H, $CF_3$, R, or OR;

n=0–2;

R=C1 to C8 alkyl, benzyl, or phenyl which can contain one or more H, D, or F; and CORx'=reactivity group.

Synthesis of α-hydroxyketos 72 with CORx'=COOH:

α-Hydroxyketos 72 with CORx'=COOH can be synthesized from ketones 69 in the same way that α-hydroxyacids 49–64 can be synthesized from ketones 1–16.

Ketones 73

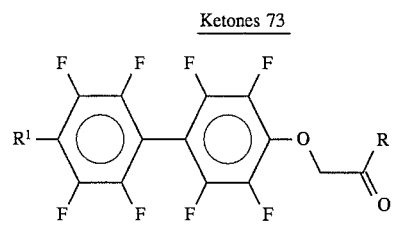

wherein $R^1$=F, $CF_3$, R, or OR; and

R=C1 to C8 alkyl, benzyl, or phenyl which can contain one or more H, D, or F.

Synthesis of ketone 73 with R=$CH_3$ and $R^1$=F:

A mixture of decafluorobiphenyl (1.67 g, 5 mmol), propargyl alcohol (0.58 ml), potassium carbonate (7.5 g), and 18-crown-6 (0.1 g) in 30 ml of toluene was stirred under reflux for 8 hours. After cooling to room temperature, 2 g of celite was added and the reaction mixture was filtered. The filtrate was evaporated on a rotavapor to remove most of the solvent and then the product was purified by preparative gas chromatography, giving 0.93 g (48%) of 4-Propargyloxynonafluorobiphenyl which was used in the next step.

To a stirred mixture of mercury sulfate (1 g) and sulfuric acid (0.1 g) in 40 ml of aqueous methanol (methanol:water= 3:1), 0.93 g of 4-propargyloxynonafluorobiphenyl in 10 ml of methanol was injected slowly at room temperature. After reflux for 2 hours, the reaction mixture was neutralized with solid sodium carbonate and then filtered. The filtrate was evaporated on a rotavapor. The residue was mixed with 30 ml of ethyl acetate and then washed with 10 ml of water. The organic layer was dried over magnesium sulfate. After the removal of most of the solvent, the product, 1-(4'-pentafluoro-phenyl)tetrafluorophenoxyacetone, was purified by preparative gas chromatography.

Similarly, other ketones 73 with other R groups can be prepared by reactions of 3-R substituted propargyl alcohols with decafluorobiphenyl or $R^1$ substituted decafluorobiphenyl followed by acidic hydrolysis as the above procedure. Ketones 73 with $R^1$=OR can also be obtained by reacting with alcohols ROH in the presence of a base.

Olefins 74

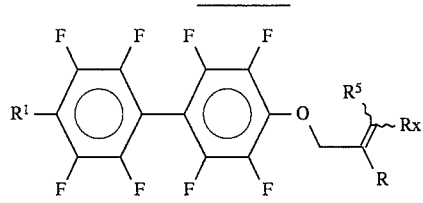

wherein $R^1$=F, $CF_3$, R, or OR;

$R^5$=H or R;

R=C1 to C8 alkyl, benzyl, or phenyl which can contain one or more H, D, or F; and Rx=reactivity group.

Synthesis of olefins 74 with Rx=COOH:

Method 1:

The olefins 74 with Rx=COOH can be synthesized from the ketones 73 in the same way that olefins 17a–32a can be synthesized from ketones 1–16.

Method 2:

The olefins 74 with R=$CH_3$ and Rx=COOH can also be prepared by reacting 4-hydroxy-4'-$R^1$-perfluorobiphenyl with ethyl 4-bromo-3-methyl-2-butenate in the presence of potassium carbonate and small amount of 18-crown-6 ether in methylene chloride, followed by hydrolysis to the corresponding acids with aqueous sodium hydroxide in methanol as described in the synthesis of olefins 66.

Glycols 75

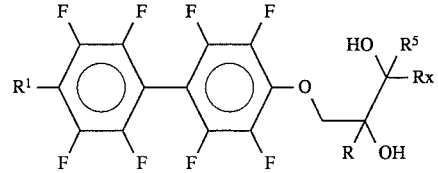

wherein $R^1$=F, $CF_3$, R or OR;

$R^5$=H or R;

R=C1 to C8 alkyl, benzyl, or phenyl which can contain one or more H, D, or F; and Rx=reactivity group.

Synthesis of Glycols 75 with Rx=COOH:

Method 1:

The glycols 75 with Rx=COOH can be synthesized directly from ketones 73 in the same way that glycols 33–48 can be synthesized directly from ketones 1–16.

Method 2:

The glycols 75 with Rx=COOH can also be synthesized from olefins 74 in the same way that glycols 33–48 can be prepared from olefin esters 17–32.

α-Hydroxyketos 76

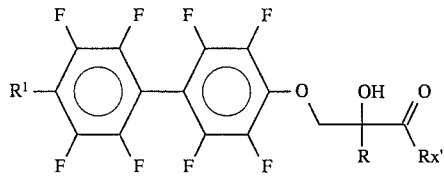

wherein $R^1$=F, $CF_3$, R, or OR;

R=C1 to C8 alkyl, benzyl, or phenyl which can contain one or more H, D, or F; and CORx'=reactivity group.

Synthesis of α-hydroxyketos 76 with CORx'=COOH:

This series of compounds with R=CH$_3$ and CORx'= COOH can be prepared from the hydrolysis of the corresponding esters of 2-methyl-2-hydroxy-3-(4,-R-tetrafluorophenyl)tetrafluorophenoxypropionic acids, which can be synthesized from the reaction of the epoxides of α-alkyl acrylic acid esters with 4-hydroxy-4'-R$^1$-octafluorobiphenyl compounds in the presence of bases by using the similar procedure as described in the syntheses of α-hydroxy acids 68.

β-Hydroxyketos as β-Hydroxyacids 77–92

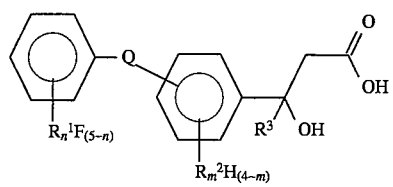

| No. | R$^1$ | R$^2$ | R$^3$ | Q |
|---|---|---|---|---|
| 77 | / | / | CH$_3$ | 4'-CH$_2$O |
| 78 | / | 3'-CH$_3$ | CH$_3$ | 4'-CH$_2$O |
| 79 | / | 3'-CH$_3$ 5'-CH$_3$ | CH$_3$ | 4'-CH$_2$O |
| 80 | / | 3'-OCH$_3$ | CH$_3$ | 4'-CH$_2$O |
| 81 | / | 3'-OCH$_3$ 5'-OCH$_3$ | CH$_3$ | 4'-CH$_2$O |
| 82 | / | 3'-F | CH$_3$ | 4'-CH$_2$O |
| 83 | / | 3'-F 5'-F | CH$_3$ | 4'-CH$_2$O |
| 84 | / | 2'-F 3'-F 5'-F | CH$_3$ | 4'-CH$_2$O |
| 85 | / | 2'-F 3'-F 5'-F 6'-F | CH$_3$ | 4'-CH$_2$O |
| 86 | / | 3'-OC$_2$H$_5$ | CH$_3$ | 5'-CH$_2$O |
| 87 | / | 3'-OCD$_3$ | CH$_3$ | 5'-CH$_2$O |
| 88 | / | 3'-OCH$_2$C$_6$F$_5$ | CH$_3$ | 5'-CH$_2$O |
| 89 | / | / | C$_2$H$_5$ | 4'-CH$_2$O |
| 90 | / | CH$_2$CH$_2$CH$_2$ | | 5'-CH$_2$O |
| 91 | / | o-Phenylene | | 4'-CH$_2$O |
| 92 | OCH$_3$ | / | CH$_3$ | 4'-CH$_2$O |

General Procedure for Synthesis of β-Hydroxy acids 77–92 from Ketones 1–16 or Olefin esters 17–32:

Method 1:

The synthesis from the Reformatsky reactions of the corresponding ketones with trimethylsilyl bromoacetate (or t-butyl bromoacetate, or other esters of bromoacetic acid) can be performed (Fürstner, A.; Synthesis, 1989, 571). For example, the reaction of 15 mmol of t-butyl bromoacetate with 10 mmol of ketones 1–16 in the presence of 20 mmol of zinc dust can be carried out in 10 ml of anhydrous tetrahydrofuran under ultrasonication for about 1 hour. After the reaction mixture is slowly poured into an ether-ice slurry with stirring, the aqueous layer is extracted with ether and then the combined organic layer is dried over magnesium sulfate. The β-hydroxy ester products can be separated by flash chromatography and then dissolved in trifluoroacetic acid and kept for 1 hour at room temperature. After the removal of the trifluoroacetic acid under reduced pressure, the corresponding β-hydroxyacid product can be obtained.

Method 2:

The synthesis from the olefins can be performed as follows: a reaction mixture of 10 mmol of the corresponding olefins (17–32) with 3.19 g (10 mmol) of mercuric acetate can be stirred in 15 ml of methanol at room temperature for 3 days. The precipitated acetoxymercury compound formed in the reaction can be collected and then dissolved in 10 ml of 2M sodium hydroxide solution. 0.2 g of sodium borohydride in 5 ml of 2M sodium hydroxide can be added at room temperature under stirring. After acidification with 5% hydrochloric acid, the aqueous solution can be decanted, saturated with sodium chloride and then extracted with ether (4×20 ml). The combined organic layer is dried over magnesium sulfate and then evaporated. The crude products can be purified by flash chromatography.

β-Hydroxyketos as β-hydroxyacids 93

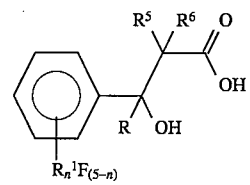

R$^1$ = H, CF$_3$, R, or OR;
R$^5$ = H or R;
R$^6$ = H or R;
n = 0–2; and
R = C1 to C8 alkyl, benzyl, or phenyl which can contain one or more of H, D, or F.

Synthesis of β-Hydroxyacids 93:

β-Hydroxyacids 93 can be synthesized from ketones 69 or olefins 70 in the same way that β-hydroxyacids 77–92 can be synthesized from ketones 1–16 or olefin esters 17–32.

β-Hydroxyketos as β-hydroxyacids 94

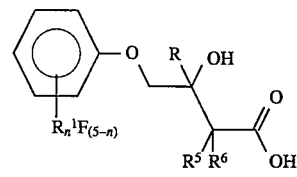

R$^1$ = H, CF$_3$, R, or OR;
R$^5$ = H or R;
R$^6$ = H or R;
n = 0–2; and
R = C1 to C8 alkyl, benzyl, or phenyl which can contain one or more of H, D, or F.

Synthesis of β-Hydroxyacids 94:

β-Hydroxyacids 94 can be synthesized from ketones 65 or olefins 66 in the same way that β-hydroxyacids 77–92 can be synthesized from ketones 1–16 or olefin esters 17–32.

β-Hydroxyketos as β-hydoxyacids 95

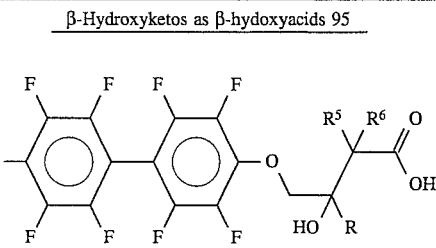

$R^1$ = F, $CF_3$, R, or OR;
$R^5$ = H or R;
$R^6$ = H or R;
R = C1 to C8 alkyl, benzyl, or phenyl which can contain one or more of H, D, or F.

Synthesis of β-Hydroxyacids 95:

β-Hydroxyacids 95 can be synthesized from ketones 73 or olefins 74 in the same way that β-hydroxyacids 77–92 can be synthesized from ketones 1–16 or olefins 17–32.

EXAMPLE V

Preferred Reactivity Groups Rx or CORx'

For olefin release tags, preferred functional groups for Rx include carboxyl (C), carboxyl active ester (e.g., N-hydroxysuccinimide ester) (CE), carbodiimide-activated carboxyl (CAC), acid chloride (AC), carbonylimidazole (CI), carbohydrazide (CH), and alkylamine (AA). These release tags and release tags with other reactivity groups can be prepared from olefins 17–32, 66, 70, and 74 by conventional procedures (e.g., Gross, E. and Meienhofer, J., Eds., *The Peptides, Vol.* 1, Academic Press, New York, 1979; Jakoby, W. B., and Wilchek, M., *Methods in Enzymology, Vol.* 34, Part B, Academic Press, New York, 1974; Pietersz, G. A., Bioconjugate Chem. 1:89–95 (1990); Lundblad, R. L., *Chemical Reagents for Protein Modification,* 2nd Ed., CRC Press, Boca Raton, 1991; Greenstein, J. P., and Winitz, M., *Chemistry of the Amino Acids,* Vol. 2, Krieger Pub. Co., Malabar, Fla., 1961).

For glycol release tags, preferred functional groups for Rx include C, CE, CAC, CI, CH, and AA. These release tags and release tags with other reactivity groups can be prepared from glycols 33–48, 67, 71 and 75 by conventional procedures (see above references).

For α-hydroxyketo and β-hydroxyketo release tags, preferred functional groups for CORx' include C, CE, CAC, CI, CH, and AA. These release tags and release tags with other reactivity groups can be prepared from α-hydroxyketos 49–64, 68, 72 and 76–95 by conventional procedures (see above references).

EXAMPLE VI

Detection of a DNA sequence

Detecting a DNA sequence can be of interest for research, clinical diagnostic, therapeutic, forensic or a related purpose. The sequence may be a gene, part of a gene, or some other region of the DNA. The sequence may be detected on the intact DNA, or after cleavage as with a restriction enzyme. Either way, the target sequence is typically blotted onto a membrane like nylon (sometimes after electrophoretic separation from most of the other DNA fragments), and exposed to a complementary strand of DNA that is labeled (the DNA probe). After the unbound DNA probe is washed away, the signal on the DNA probe is measured.

A DNA probe is commonly obtained by nick translation or by automated synthesis (Kricka, L. J., ed., Nonisotopic DNA Probe Techniques, Academic Press, San Diego, Calif., 1992). In the former case, a deoxynucleotide triphosphate monomer bearing a release tag can be used which is synthesized in the same way that a biotin-labeled deoxynucleotide triphosphate is obtained (Kricka, Ibid.). In the latter case, a 5'-amino labeled DNA probe can be synthesized using commercially available compounds, and then reacted with a release tag N-hydroxysuccinimide ester, or with a carbodiimide-activated release tag, in the same way that other carboxylic tags have been attached to 5'-amino labeled DNA probes (Kricka, Ibid.). The release tag DNA probe is next employed in the hybridization assay in the same way as other DNA probes. The DNA probe, once hybridized to the target DNA, can be detected by releasing the ketone signal compound directly, or after the DNA probe is first washed off the target, e.g. with hot water containing sodium dodecylsulfate. The following conditions can be used to release the electrophoric signal ketone: aqueous permanganate for an olefin release tag; aqueous periodate for a glycol release tag; aqueous periodate for an α-hydroxyketo release tag; and heat for a β-hydroxyketo release tag or for a glycol release tag in which the glycol OH closest to the signal group is also β to a keto moiety. The ketone can then be detected by volatilizing it thermally into an instrument like a GC-ECNI-MS or GC-ECD. A laser may be used to provide the thermal energy for the volatilization, and also for the prior thermal release. The ketone may be volatilized by first dissolving it in a volatile organic solvent like isooctane, methanol or toluene and then injecting this solution into the GC-ECNI-MS or GC-ECD. Because of the multiplicity of electrophoric release tags, each of many DNA probes can be labeled with a unique release tag (in terms of the signal group), and then combined for use as a cocktail to conduct many hybridization reactions simultaneously on a given sample of target DNA.

EXAMPLE VII

Detection of an antigen

For a given antigen, two antibodies (designated here I and II) are obtained that can bind simultaneously to the antigen so that a solid phase sandwich immunoassay can be set up to detect the antigen. First antibody I is immobilized on a solid phase, e.g. by adsorption onto the surface of a well in a polystyrene microtiter plate. Antibody II is labeled with a release tag in the same way that it can be labeled with a related tag like biotin, e.g. by reaction with a release tag NHS ester under aqueous conditions near pH 7 in HEPES buffer. The antigen is then detected by adding it along with (or prior to) a release tag-labeled antibody II to the microtiter well in aqueous buffer, incubating, washing away unbound release tag-antibody II, releasing the ketone as in Example VI, and detecting the ketone as in Example VI. An antigen on a cell or microorganism (e.g. virus, bacterium) can be detected by using a complementary antibody labelled with a release tag, and many such antigens can be detected simultaneously by using a cocktail of such labeled antibodies.

EXAMPLE VIII

Detection of a hapten

If the hapten (e.g. drug, pesticide, metabolite, hormone or other small molecule) does not possess a functional group like a hydroxy or amino that can be labeled with a release tag, then an analog of the hapten must be synthesized or obtained that possesses such a group. An antibody is obtained which binds the hapten by immunizing an animal with a hapten-protein or analog-protein conjugate. A competitive immunoassay is set up in which comparable amounts of free hapten (to be measured) and release tag-labeled hapten compete for binding to a limited amount of the antibody. After equilibrium has been attained, separation of free and antibody-bound release tag-hapten is done in a standard way, e.g. with charcoal, polyethylene glycol, or solid-phase second antibody. The free or antibody-bound hapten is measured as in Examples VI and VII, which provides, relying on a standard curve, a measure of the free hapten.

EXAMPLE IX

Labeling detection of an analyte

An analyte may possess a functional group like carboxy, hydroxy, amino, sulfhydryl, or aldehyde that can be covalently labeled, making it possible to detect the analyte via direct labeling with a release tag. Another analyte, which may lack such a group, can be chemically transformed to possess such a group, and then be similarly detected via such labeling. A release tag is selected which possesses a reactivity group that is capable of forming a covalent bond to the complementary functional group on the analyte. Since glycol, $\alpha$-hydroxyketo and $\beta$-hydroxyketo release tags possess a hydroxy group, such tags would not be used to label an analyte possessing a hydroxy functional group. Appropriate combination of analyte functional groups and release tag reactivity groups are as follows: carboxy analyte/amino or hydrazide reactivity group on the release tag; hydroxy analyte/acid chloride; bromobenzyl or epoxy reactivity group on an olefin release tag; amino analyte/carboxy (activated, as with a carbodiimide), carboxy active ester (e.g. N-hydroxysuccinimide ester), or aldehyde reactivity group; sulfhydryl analyte/bromoacetyl or maleimido reactivity group; and aldehyde analyte/amino or hydrazide reactivity group. In the overall analytical procedure, the analyte typically is first partly purified by extraction, chromatography, electrophoresis or a combination of these techniques. The analyte is then covalently labeled with the release tag as defined above. Additional purification of the sample including, removal of residual release tag, is accomplished by extraction, chromatography, electrophoresis or a combination of these techniques. The release tag-labeled analyte is then detected as in Example VI by releasing and detecting the ketone signal group.

In all of these examples, a polymeric form of the release tag may be employed to increase the sensitivity. For example, many copies of a given release tag may be attached to nucleic acid, polysaccharide, synthetic polymer or polypeptide, and the resulting polymeric release tag, in turn, can be attached to the DNA probe, antibody, antigen, or analyte.

EXAMPLE X

Thermal release of a ketone

Figure 2:
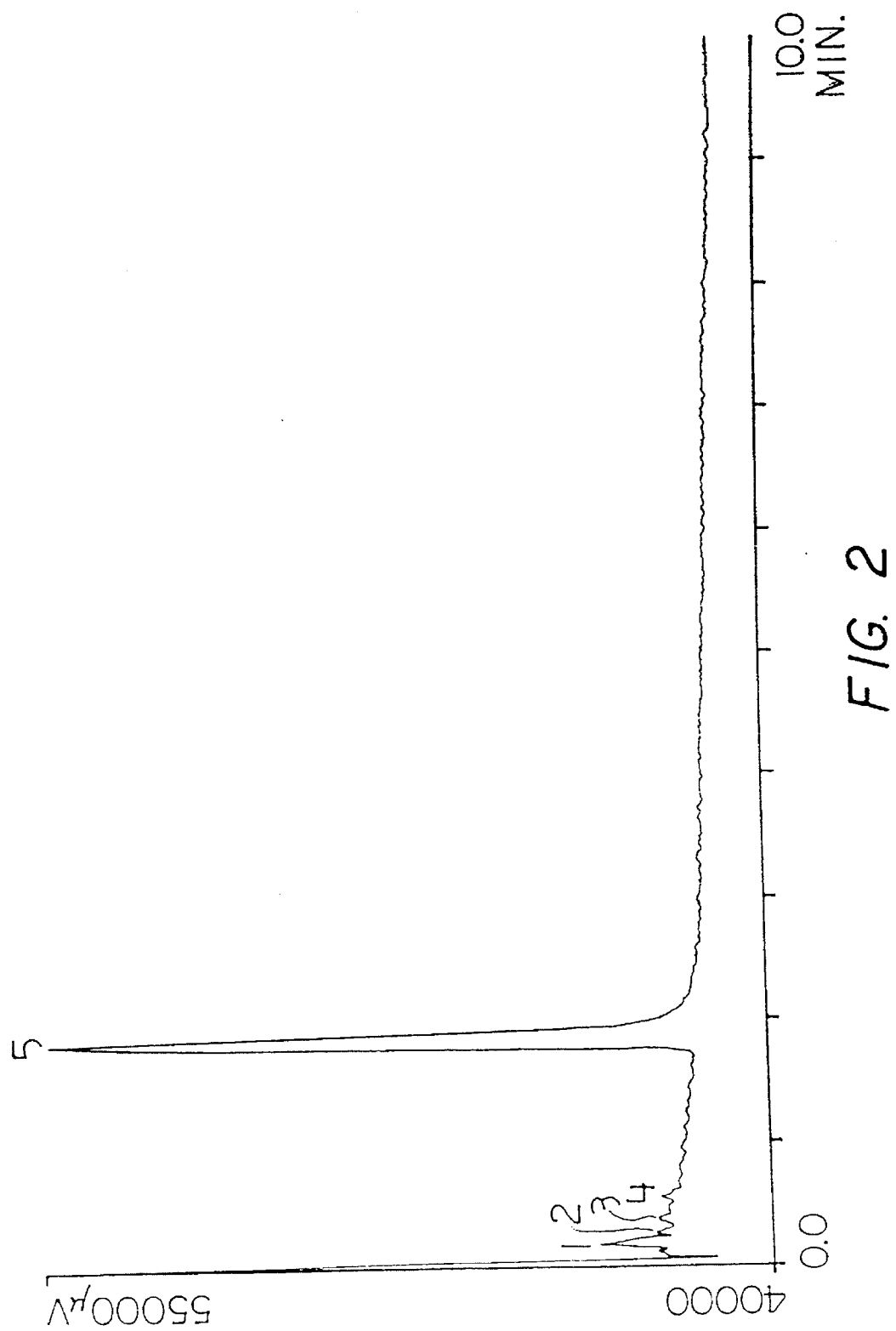
FIG. 2 shows a gas chromatography chromatogram of an authentic signal compound of the invention.

1) Release in a GC column. One µl of the methyl ester of 78 in methanol (140 pg/µl, 333 fmol/µl) was on-column injected at 250° C. into a HP Ultra-2 12 m×0.32 mm×0.54 µm column (column temperature: 160° C.) and detected as ketone 2 (3'-methyl-4'-pentafluorobenzyloxyacetophenone) (80% yield) by an electron capture detector (340° C.). The resulting GC chromatogram is given in FIG. 1. FIG. 2 shows the GC chromatogram from the injection of 1 µl of a methanolic solution of authentic ketone 2 (110 pg/µl, 333 fmol/µl). Similar results can also be obtained using a GC-ECNI-MS.

2) Release in a glass tube. One µl of the methyl ester of 78 was sealed into a melting point tube and then was suspended over refluxing dihydroxyethyl ether (b.p. 245° C., measured 225° C.) for 2 min. After 20 µl of acetonitrile was added, the sample was analyzed by HPLC, giving a peak for ketone 2. Only a trace of 78 (<2%) could be observed. Similarly, suspending 78 over refluxing ethylene glycol (b.p. 196°–8° C., measured 195° C.) for 5 min afforded >95% of ketone 2 by HPLC. After 20 min of suspension over refluxing ethylene glycol, no 78 remained. The released ketone can also be detected by reacting the acetonitrile solutions into a GC-ECD or GC-ECNI-MS.

EXAMPLE XI

A release tag with Rx=N-hydroxysuccinimide ester is reacted with glycine methyl ester (as a linking reagent) in aqueous HEPES buffer at pH 7.0. The methyl ester then is hydrolyzed with aqueous, methanolic NaOH, and reacted with N,N-carbonyldiimidazole to form release tag-glycine. Alternatively the original release tag can be reacted in HEPES buffer at pH 7.5 with ethylenediamine (as a linking reagent), to form release tag-ethylenediamine. Alternatively the original release tag can be reacted with lysozyme (as a linking reagent), to form (release tag)$_n$-lysozyme where $n \geq 8$. Alternatively the release tag can be reacted with nitrous acid-oxidized glycol chitosan (as a linking reagent; Guan, K., Cecchini, D.and Giese, R. W., Carbohydrate Res., in press) to form (release tag)$_n$-Chitin Leash where $n \geq 5$.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. In an assay which includes contacting an analyte-containing sample with a labeled reagent, or with a conjugate made by covalently reacting a labeled reagent with standard said analyte, or with an analog of, ligand for, or specific binding partner of said analyte, incubating said contacted sample, and measuring the amount of label, the improvement which comprises:

using as the labeled reagent a release tag compound, S-Re-Rx, wherein S is a signal group covalently bound to group Re, and Re is a cleavable release group which is covalently bound to group Rx which is a reactivity group;

and S is further defined as comprising a halogenated electron-absorbing group which can be measured by electron capture detection;

and Re is further defined as comprising a functionality selected from the group consisting of $\alpha$-hydroxyketos and $\beta$-hydroxyketos, and is capable of releasing the signal group in a volatile form suitable for measuring by electron capture detection;

and Rx is further defined as comprising a functional group which is capable of forming a covalent bond with another molecule.

2. In an assay which includes contacting an analyte-containing sample with a labeled reagent, or with a conjugate made by covalently reacting a labeled reagent with standard said analyte, or with an analog of ligand for, or specific binding partner of said analyte, incubating said contacted sample, and measuring the amount of label, the improvement which comprises:

using as the labeled reagent a release tag compound, S-Re-Rx, wherein S is a signal group covalently bound to group Re, and Re is a cleavable release group which is covalently bound to group Rx which is a reactivity group;

and S is further defined as comprising a halogenated electron-absorbing group which can be measured by electron capture detection;

and Re is further defined as comprising a functionality cleavable by heat and is capable of releasing the signal group in a volatile form suitable for measuring in the gas phase;

and Rx is further defined as comprising a functional group which is capable of forming a covalent bond with another molecule;

said improvement further comprising measuring the amount of label following thermal release of the signal group.

3. The assay of claim 2 wherein Re is a β-hydroxyketo group.

4. The assay of claim 2 wherein Re is an α,β-dihydroxyketo group.

5. The assay of claim 2 wherein said signal group is released as a ketone compound.

6. The assay of claim 2 wherein said signal group is released as a polyfluorinated ketone compound.

7. The assay of claim 1 wherein Re is an α,β-dihydroxyketo group.

8. The assay of claim 1 wherein said signal group is released as a ketone compound.

9. The assay of claim 1 wherein said signal group is released as a polyfluorinated ketone compound.

* * * * *

UNITED STATES PATENT AND TRADEMARK OFFICE
CERTIFICATE OF CORRECTION

PATENT NO : 5,610,020
DATED : March 11, 1997
INVENTOR(S): Roger W. Giese, et al.

It is certified that error appears in the above-identified patent and that said Letters Patent is hereby corrected as shown below:

Column 12, line 66, "ppm:" should read --ppm;--.

Column 13, line 37, "with fine splitting, $CH_2O$)," should read --with fine splitting, 2H, $CH_2O$),--.

Column 14, line 66, ($J_{C-F}$=249 Hz, C2'),C3'),-- should read --$^2J_{C-F}$=7 Hz, C3'),--.

Column 33, line 1, claim 2, "analog of ligand for," should read --analog of, ligand for--.

Signed and Sealed this

Fourth Day of January, 2000

Attest:

Attesting Officer

*Acting Commissioner of Patents and Trademarks*